United States Patent
Kurn et al.

(10) Patent No.: US 7,176,025 B2
(45) Date of Patent: Feb. 13, 2007

(54) METHODS FOR GENERATING DOUBLE STRANDED DNA COMPRISING A 3' SINGLE STRANDED PORTION AND USES OF THESE COMPLEXES FOR RECOMBINATION

(75) Inventors: Nurith Kurn, Palo Alto, CA (US); Martin Junhong Wang, Foster City, CA (US)

(73) Assignee: Nugen Technologies, Inc., San Carlos, CA (US)

( * ) Notice: Subject to any disclaimer, the term of this patent is extended or adjusted under 35 U.S.C. 154(b) by 501 days.

(21) Appl. No.: 10/386,623

(22) Filed: Mar. 11, 2003

(65) Prior Publication Data

US 2003/0215926 A1 Nov. 20, 2003

Related U.S. Application Data

(60) Provisional application No. 60/363,729, filed on Mar. 11, 2002.

(51) Int. Cl.
  C12N 15/00 (2006.01)
  C12Q 1/68 (2006.01)
  C07H 21/02 (2006.01)
  C07H 21/04 (2006.01)

(52) U.S. Cl. .................. 435/440; 435/6; 536/23.1; 536/24.3

(58) Field of Classification Search .................. 435/6, 435/440; 536/23.1, 24.3
See application file for complete search history.

(56) References Cited

U.S. PATENT DOCUMENTS

| | | | |
|---|---|---|---|
| 4,876,187 A | 10/1989 | Duck et al. |
| 5,043,272 A | 8/1991 | Hartley |
| 5,130,238 A | 7/1992 | Malek et al. |
| 5,169,766 A | 12/1992 | Schuster et al. |
| 5,262,311 A | 11/1993 | Pardee et al. |
| 5,399,491 A | 3/1995 | Kacian et al. |
| 5,403,711 A | 4/1995 | Walder et al. |
| 5,427,929 A | 6/1995 | Richards et al. |
| 5,480,784 A | 1/1996 | Kacian et al. |
| 5,554,516 A | 9/1996 | Kacian et al. |
| 5,554,517 A | 9/1996 | Davey et al. |
| 5,665,545 A | 9/1997 | Malek et al. |
| 5,679,512 A | 10/1997 | Laney et al. |
| 5,683,879 A | 11/1997 | Laney et al. |
| 5,700,642 A | 12/1997 | Monforte et al. |
| 5,744,308 A | 4/1998 | Guillou-Bonnici et al. |
| 5,811,238 A | 9/1998 | Stemmer et al. |
| 5,824,517 A | 10/1998 | Cleuziat et al. |
| 5,824,518 A | 10/1998 | Kacian et al. |
| 5,830,655 A | 11/1998 | Monforte et al. |
| 5,830,721 A | 11/1998 | Stemmer et al. |
| 5,849,542 A | 12/1998 | Reeve et al. |
| 5,876,976 A | 3/1999 | Richards et al. |
| 5,888,779 A | 3/1999 | Kacian et al. |
| 5,958,681 A | 9/1999 | Wetmur et al. |
| 5,962,271 A | 10/1999 | Chenchik et al. |
| 5,962,272 A | 10/1999 | Chenchik et al. |
| 5,965,409 A | 10/1999 | Pardee et al. |
| 6,027,923 A | 2/2000 | Wallace |
| 6,030,774 A | 2/2000 | Laney et al. |
| 6,037,152 A | 3/2000 | Richards et al. |
| 6,087,103 A | 7/2000 | Burmer |
| 6,132,997 A | 10/2000 | Shannon |
| 6,251,639 B1 | 6/2001 | Kurn |
| 6,280,935 B1 | 8/2001 | Macevicz |
| 6,306,365 B1 | 10/2001 | Ruoslahti et al. |
| 6,309,842 B1 | 10/2001 | Dower et al. |
| 6,319,714 B1 | 11/2001 | Crameri et al. |
| 6,335,160 B1 | 1/2002 | Patten et al. |
| 6,344,356 B1 | 2/2002 | Stemmer |
| 6,358,712 B1 | 3/2002 | Jarrell et al. |
| 6,692,918 B2 | 2/2004 | Kurn |
| 6,794,138 B1 * | 9/2004 | Cao et al. ..................... 435/6 |
| 2001/0000077 A1 | 3/2001 | Engelhardt et al. |
| 2001/0034048 A1 | 10/2001 | Kurn |
| 2001/0041334 A1 | 11/2001 | Rashtchian et al. |
| 2002/0058270 A1 | 5/2002 | Kurn |
| 2003/0017591 A1 | 1/2003 | Kurn |
| 2003/0087251 A1 | 5/2003 | Kurn |
| 2003/0186234 A1 | 10/2003 | Kurn |

FOREIGN PATENT DOCUMENTS

| | | |
|---|---|---|
| EP | 0 365 627 | 5/1990 |
| EP | 0 395 398 | 10/1990 |
| EP | 0 497 272 | 8/1992 |
| EP | 0 500 224 | 8/1992 |
| EP | 0 543 612 | 5/1993 |
| EP | 0 667 393 | 8/1995 |
| EP | 0 878 553 | 11/1998 |
| WO | WO 00/08208 | 2/2000 |
| WO | WO 00/40715 | 7/2000 |
| WO | WO 00/52191 | 9/2000 |
| WO | WO 01/20035 | 3/2001 |
| WO | WO 01/23613 | 4/2001 |
| WO | WO 01/064952 | 9/2001 |
| WO | WO 02/00938 | 1/2002 |
| WO | WO 02/028876 | 4/2002 |
| WO | WO 02/48402 | 6/2002 |
| WO | WO 02/072772 | 9/2002 |
| WO | WO 02/103013 | 12/2002 |
| WO | WO 03/078645 | 9/2003 |
| WO | WO 03/083435 | 10/2003 |

OTHER PUBLICATIONS

Barbas III, C.F. et al.(1994). "*In Vitro* Evolution of a Neutralizing Human Antibody to Human Immunodeficiency Virus Type I to Enhance Affinity and Broaden Strain Cross-Reactivity," *Proc. Natl. Acad. Sci. USA* 91:3809-3813.

(Continued)

*Primary Examiner*—Ethan Whisenant
(74) *Attorney, Agent, or Firm*—Morrison & Foerster LLP

(57) ABSTRACT

Methods of recombining nucleic acids are provided. In particular, methods for the production of partially double stranded nucleic acids comprising a 3' overhang from an RNA target and use in methods of recombining polynucleotides is described. These methods do not require thermocycling. The present invention also provides methods of recombining and selection which allow for identification of proteins comprising improved or desired characteristics.

32 Claims, 8 Drawing Sheets

OTHER PUBLICATIONS

Coco, W.M. et al. (2001). "DNA Shuffling Method for Generating Highly Recombined Genes and Evolved Enzymes," *Nature Biotechnology*. 19:354-359.

Coljee, V.W. et al. (2000). "Seamless Gene Engineering Using RNA- and DNA- Overhang Cloning," *Nature Biotechnology* 18:789-791.

Crameri, A. et al. (1997). "Molecular Evolution of an Arsenate Detoxification Pathway by DNA Shuffling," *Nature Biotechnology* 15:436-438.

Go, M. (1985). "Protein Structures and Split Genes," *Adv. Biophys.* 19:91-131.

Gubler, U. et al. (1983). "A Simple and Very Efficient Method for Generating cDNA Libraries," *Gene* 25:263-269.

Gulick, A.M. et al. (1995). "Forced Evolution of Glutathione S-Transferase to Create a More Efficient Drug Detoxication Enzyme," *Proc. Natl. Acad. Sci. USA* 92:8140-8144.

Heim, R. et al. (1996). "Engineering Green Fluorescent Protein for Imporved Brightness, Longer Wavelengths and Fluorescence Resonance Energy Tranfer," *Curr. Biol.* 6:178-182.

Joyce, G.F. (1992). "Directed Molecular Evolution," *Scientific American* 267(6):90-97.

Kikuchi, M. et al. (1999). "Novel Family Shuffling Methods for the *in vitro* Evolution of Enzymes," *Gene* 236:159-167.

Kikuchi, M. et al. (2000). "An Effective Family Shuffling Method Using Single-Stranded DNA," *Gene* 243:133-137.

Kolkman, J.A. et al. (2001). "Directed Evolution of Proteins by Exon Shuffling," *Nature Biotechnology* 19:423-428.

Kurtzman, A.L. et al. (2001). "Advances in Directed Protein Evolution by Recursive Genetic Recombination: Applications to Therapeutic Proteins," *Current Opinion in Biotechnology* 12:361-370.

Okayama, H. et al. (1982). "High-Efficiency Cloning of Full-Lengh cDNA," *Molecular and Cellular Biology* 2(2):161-170.

Plückthun, A. et al. (2001). "*In Vitro* Selection and Evolution of Proteins," *Advances in Protein Chem.* 55:367-403.

Schmidt-Dannert, C. (2001). "Directed Evolution of Single Proteins, Metabolic Pathways, and Viruses," *Biochemistry* 40(44):13125-13136.

Stemmer, W.P.C. (1994). "Rapid Evolution of a Protein *In Vitro* by DNA Shuffling," *Nature* 370:389-391.

Stemmer, W.P.C. (1994). "DNA Shuffling by Random Fragmentation and Reassembly: *In Vitro* Recombination for Molecular Evolution," *Proc. Natl. Acad. Sci. USA* 91:10747-10751.

Traut, T.W. (1986). "Are Proteins Made of Modules?," *Molecular and Cellular Biochemistry* 70:3-10.

Volkov, A.A. et al. (1999). "Recombination and Chimeragenesis by *in vitro* Heteroduplex Formation and *in vivo* Repair," *Nucleic Acids Research* 27(18):e18i-e18vi.

You, L. et al. (1994). "Directed Evolution of Subtilisin E in *Bacillus subtilis* to Enhance Total Activity in Aqueous Dimethylformamide," *Protein Eng.* 9(1):77-83.

Zhang, Ji-Hu. et al. (1997). "Directed Evolution of a Fucosidase From a Galactosidase by DNA Shuffling and Screening," *Proc. Natl. Acad. Sci. USA* 94:4504-4509.

Arashi-Heese, N. et al. (1999). "*Xcm*I Site-Containing Vector for Direct Cloning and In Vitro Transcription of PCR Product," *Molecular Biotechnology* 12:281-283.

International Search Report mailed on Jan. 8, 2004, for PCT patent application No. PCT/US03/07425 filed on Mar. 11, 2003, four pages.

* cited by examiner

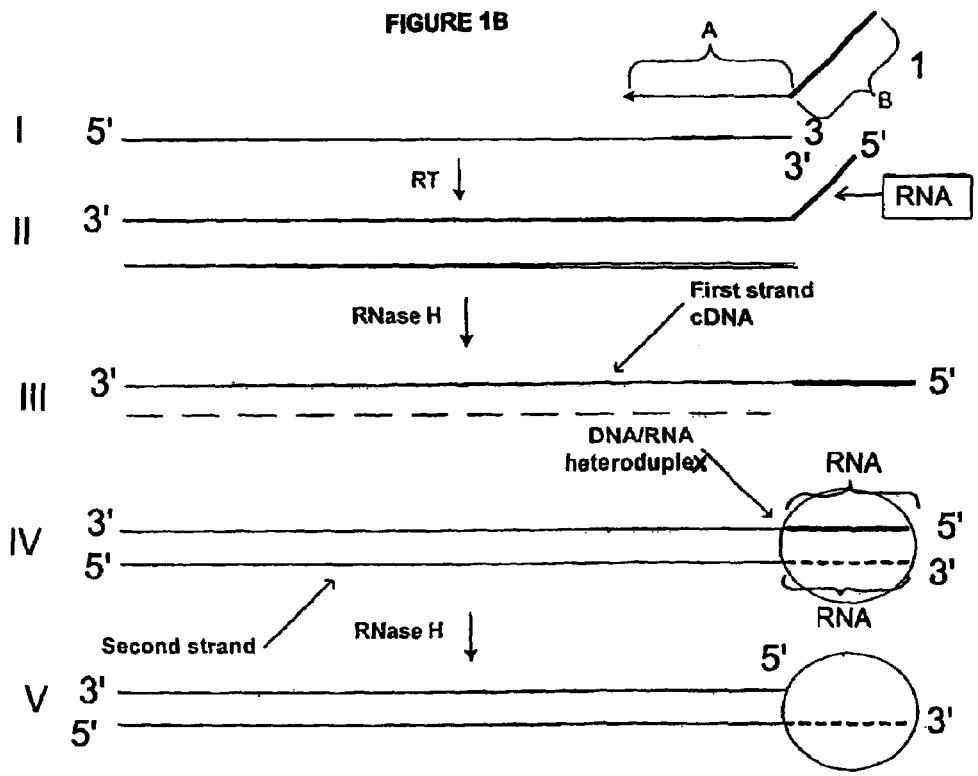

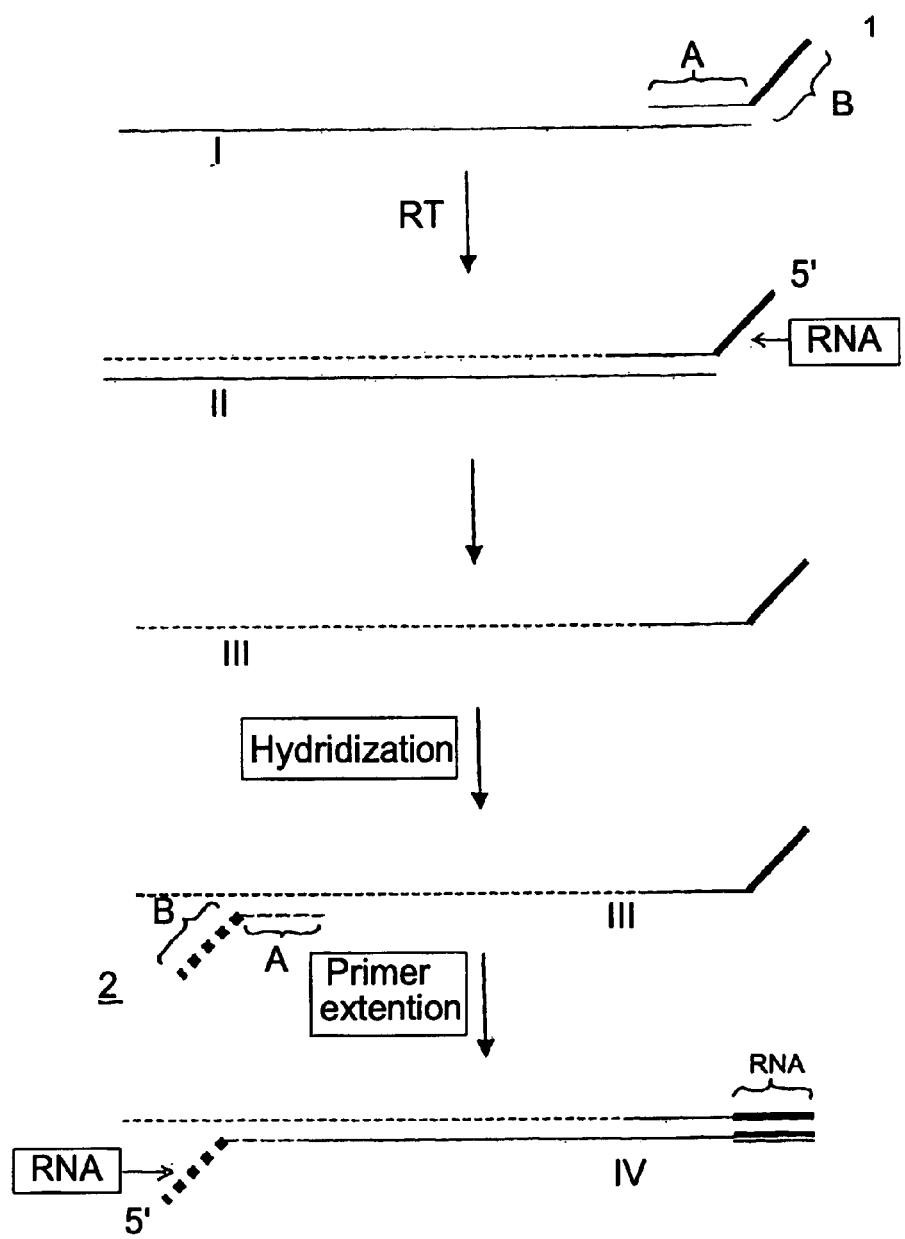

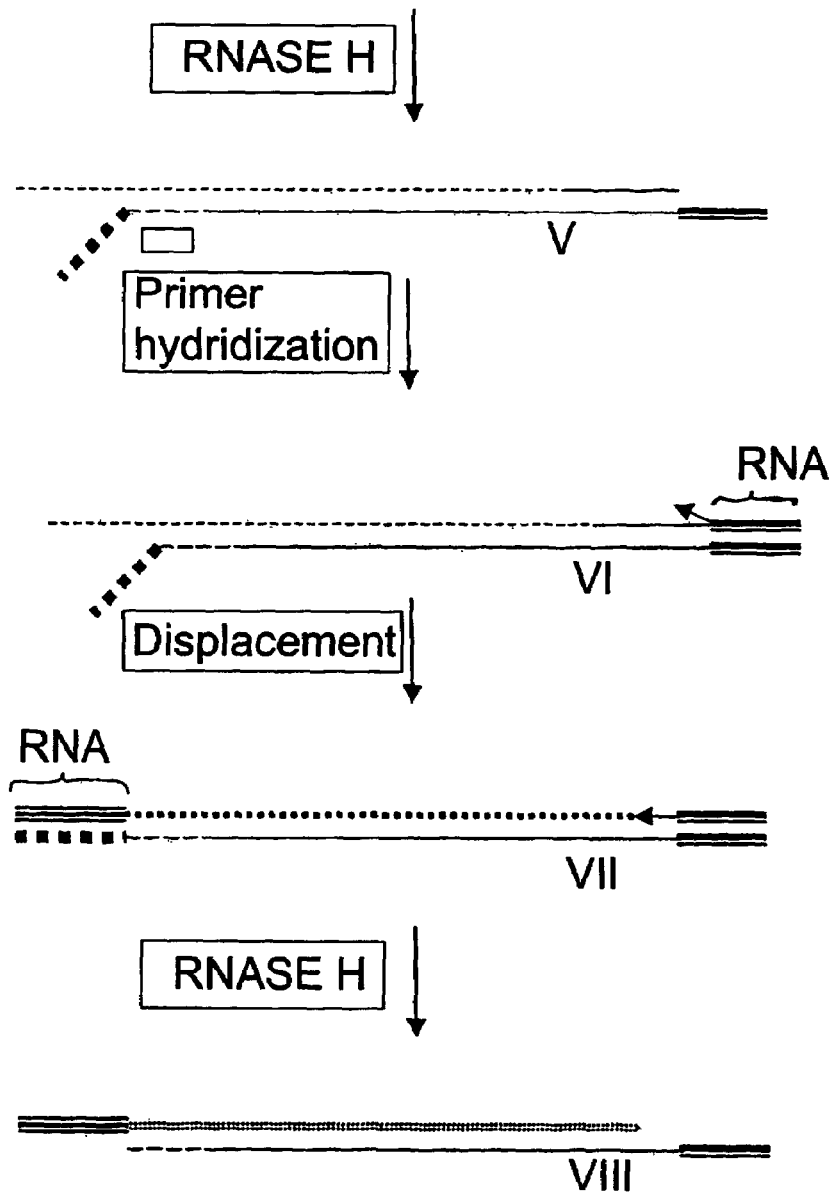

FIGURE 5
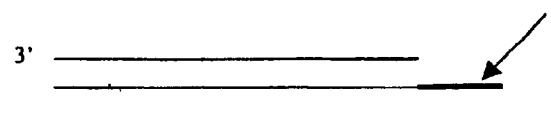
3' Plurality of Double stranded cDNA with random 3'-overhang
Hybridization of the random single stranded 3' overhangs of the various cDNA sequences at low stringency condition in the presence of DNA polymerase with or without strand displacement activity.
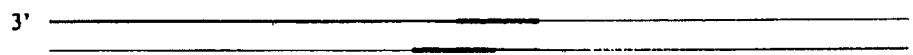
3'
3'
Recombined products

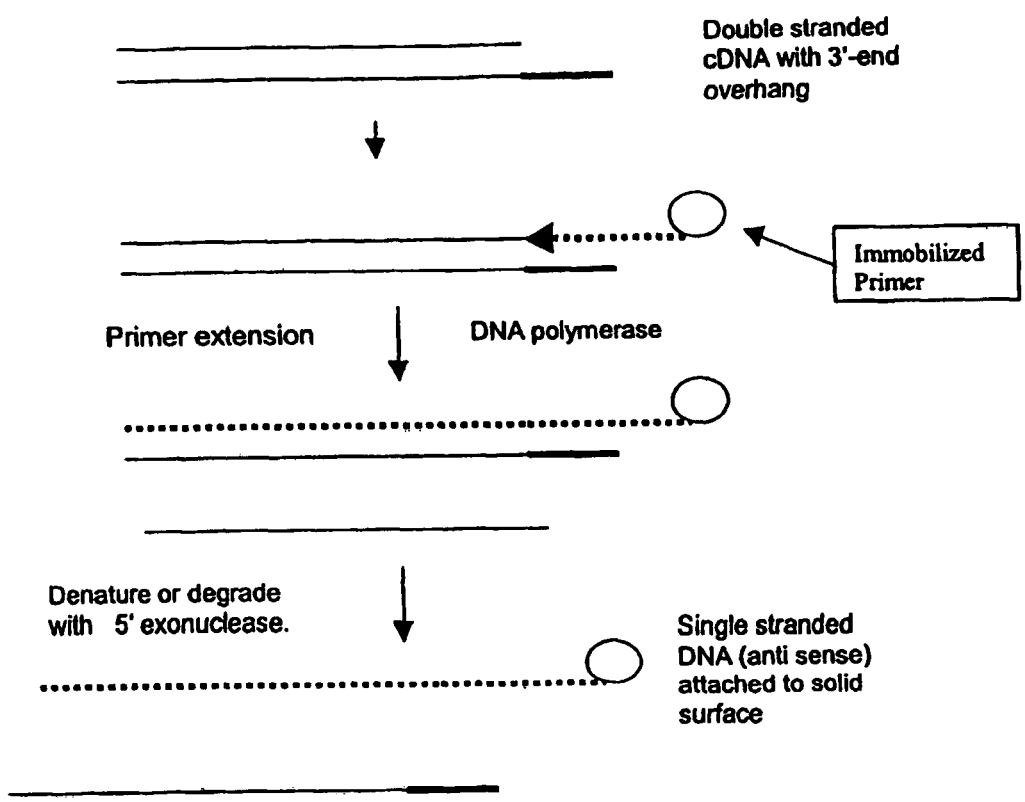

METHODS FOR GENERATING DOUBLE STRANDED DNA COMPRISING A 3' SINGLE STRANDED PORTION AND USES OF THESE COMPLEXES FOR RECOMBINATION

CROSS REFERENCE TO RELATED APPLICATIONS

This application claims the priority benefit of provisional application U.S. Ser. No. 60/363,729, filed Mar. 11, 2002, the contents of which are incorporated by reference in their entirety.

TECHNICAL FIELD

The present invention relates to methods and compositions for generating hybridized first and second primer extension product comprising a 3' single stranded portion, from RNA template, and uses for these complexes in recombination methods. In one aspect, the invention provides methods, which do not require thermocycling, for generating recombined polynucleotides useful for screening and/or selection of a desired phenotype and/or encoding a protein having an advantageous predetermined property.

BACKGROUND ART

There has been a rapid and steady progress in the ability to clone and recombine DNA molecules in recent years. These advances began with the discovery of restriction enzymes that were capable of cleaving double-stranded DNA, so that DNA fragments were produced that could be recombined to generate new recombinant molecules. The revolution was extended by the discovery and development of the polymerase chain reaction (PCR), which allowed rapid amplification of particular DNA segments, producing large amounts of material that could be subsequently cleaved and recombined with other DNA molecules.

Despite the power of these digestion and amplification techniques, however, there remains substantial room for improvement. Restriction enzymes are expensive and sometimes inefficient or available in crude, contaminated preparations. Further, PCR amplification often yields products that are refractory to direct cloning, due to addition of a terminal 3'-dAMP residue by many thermophilic DNA polymerases, including Taq, the most commonly-used enzyme for PCR.

Particularly desirable systems would generate hybrid products suitable for nucleic acid recombination with minimal reliance on restriction enzymes, would provide for efficient recombination, and would be generally useful for recombination between nucleic acids having a wide variety of chemical structures.

Jarrell et al, see WO 00/40715 and U.S. Pat. No. 6,358,712, teach methods for library assembly involving generation of double stranded products with 3' or 5' overhangs. However, this method uses polymerase chain reaction, thus requiring thermal cycling and exponential amplification. Furthermore, Jarrell discloses use of a double stranded DNA as template.

Methods using production of recombined products include molecular evolution and "DNA shuffling". Molecular evolution is a powerful tool for producing novel proteins with enhanced or unique selectable properties. Proteins with enhanced enzymatic activity, enhanced thermal stability, or enhanced stability in organic solvents or defined media such as alkaline or high salt media, novel enzymatic activity, or other desired features may be produced by recombining pieces of mutagenized variants of a single gene or pieces of different genes to form hybrid proteins. In general, in vitro directed evolution involves generation of hybrid polynucleotides, amplification of the polynucleotides, and screening to select a protein having the desired property or properties. "DNA shuffling" involves mutagenesis of a single gene rather than reassembly of multiple domains from related genes. Known methods for DNA shuffling include mutagenesis of a gene, selection of mutants, fragmentation by DNase I, and recombination of the fragments in vitro using PCR (Stemmer, *Proc. Natl. Acad. Sci.* 91:10747–51 (1994); Stemmer, *Nature* 370:389–91 (1994)).

Analyses have revealed that many proteins are composed of a number of discrete domains. The individual domains of such a protein are often involved in specific functions that contribute to the protein's overall activity. A number of domains have been found to be evolutionarily mobile. Mobile domains are characterized by their ability to fold independently. "Mosaic proteins" that include multiple mobile domains have been characterized and appear to have arisen through evolution by "exon shuffling." The natural process of exon shuffling can be mimicked in vitro by generating and screening libraries of exon shuffled genes (Kolkman and Stemmer, *Nature Biotechnology* 19:423–28 (2001)). The domain-encoding exons in such libraries may be from closely related or divergent genes. Further, domain-encoding exons may be derived from related genes from the same species or homologs from closely-related species.

Thus, there is a serious need for methods of generating double stranded nucleic acid sequences comprising at least one defined single stranded DNA portion, where the double stranded nucleic acid sequences are generated from RNA using methods which do not require and thus avoid thermocycling, and where the double stranded nucleic acid sequences can be random, can be selected from a pool of all mRNA sequences, or can be selected from a related sequences (e.g., all sequences encoding a particular domain, sequences encoding members of a superfamily of genes, and the like).

All references cited herein, including patent applications and publications, are incorporated by reference in their entirety.

DISCLOSURE OF THE INVENTION

In one aspect, the invention provides methods for an aspect leading to generating a complex of first and second primer extension product, said complex comprising a 3' single stranded portion useful for recombining nucleic acids, said methods comprising: (a) preparing a complex of first and second primer extension products said complex comprising a 3' single stranded portion, wherein said complex of first and second primer extension products is prepared according to a method comprising: (i) extending a first primer hybridized to a target RNA with RNA-dependent DNA polymerase (an enzyme comprising RNA-dependent DNA polymerase activity), wherein the first primer is a composite primer comprising an RNA portion and a 3' DNA portion, whereby a complex comprising a first primer extension product and the target RNA is produced; (ii) cleaving RNA in the complex of step. (i) (cleavage may be effected, for example, with an enzyme that cleaves RNA from an RNA/DNA hybrid); (iii) extending a second primer hybridized to the first primer extension product using a DNA dependent polymerase (which, as described herein, can comprise an RNA dependent DNA polymerase activity, or can comprise a DNA dependent DNA polymerase and an RNA dependent polymerase; thus, extension involves using an enzyme comprising DNA-dependent DNA polymerase activity and an enzyme comprising RNA-dependent DNA polymerase activity, which as described herein may be in same or separate enzymes), whereby a second primer extension product is produced to form a complex of first and second primer extension products; (iv) cleaving RNA from the composite primer in the complex of step (iii) with an enzyme that cleaves RNA from an RNA/DNA hybrid such that a complex comprising hybridized first and second primer extension product comprising a 3' single stranded DNA portion is generated. In some embodiments, cleavage of step (ii) is effected using an enzyme that cleaves RNA from an RNA/DNA hybrid. In some embodiments, the enzyme is RNaseH.

In one aspect, the invention provides methods for an aspect leading to recombining nucleic acids (making a hybrid), said methods comprising: hybridizing a 3' single stranded portion of a complex of first and second primer extension products with a recipient nucleic acid molecule; whereby a hybrid nucleic acid is generated.

In another aspect, the invention provides methods for an aspect leading to recombining nucleic acids (making a hybrid), said methods comprising: hybridizing a 3' single stranded portion of a complex of first and second primer extension products with a recipient nucleic acid molecule, whereby a hybrid nucleic acid is generated, wherein said complex of first and second primer extension products is prepared according to a method comprising: (i) extending a first primer hybridized to a target RNA with an enzyme comprising RNA-dependent DNA polymerase activity, wherein the first primer is a composite primer comprising an RNA portion and a 3' DNA portion, whereby a complex comprising a first primer extension product and the target RNA is produced; (ii) cleaving RNA in the complex of step (i) (cleavage may be effected, for example, with an enzyme that cleaves RNA from an RNA/DNA hybrid); (iii) extending a second primer hybridized to the first primer extension product with an enzyme comprising DNA-dependent DNA polymerase activity and an enzyme comprising RNA-dependent polymerase activity, whereby a second primer extension product is produced to form a complex of first and second primer extension products; (iv) cleaving RNA from the composite primer in the complex of step (iii) with an enzyme that cleaves RNA from an RNA/DNA hybrid such that a complex comprising hybridized first and second primer extension product comprising a 3' single stranded DNA portion is generated. In some embodiments, cleavage of step (ii) is effected using an enzyme that cleaves RNA from an RNA/DNA hybrid. In some embodiments, the enzyme is RNaseH.

In one aspect, the invention provides methods for recombining nucleic acids, said methods comprising: (a) preparing a complex of first and second primer extension products said complex comprising a 3' single stranded portion, wherein said complex of first and second primer extension products is prepared according to a method comprising: (i) extending a first primer hybridized to a target RNA with an enzyme comprising RNA-dependent DNA polymerase activity, wherein the first primer is a composite primer comprising an RNA portion and a 3' DNA portion, whereby a complex comprising a first primer extension product and the target RNA is produced; (ii) cleaving RNA in the complex of step (i) (cleavage may be effected, for example, with an enzyme that cleaves RNA from an RNA/DNA hybrid); (iii) extending a second primer hybridized to the first primer extension product with an enzyme comprising DNA-dependent DNA polymerase activity and RNA-dependent DNA polymerase activity, whereby a second primer extension product is produced to form a complex of first and second primer extension products; (iv) cleaving RNA from the composite primer in the complex of step (iii) with an enzyme that cleaves RNA from an RNA/DNA hybrid such that a complex comprising hybridized first and second primer extension product comprising a 3' single stranded DNA portion is generated; (b) hybridizing the 3' single stranded portion of the complex of first and second primer extension products with a recipient nucleic acid molecule; whereby a hybrid nucleic acid is generated; and (c) generating a recombined nucleic acid from the hybrid nucleic acid. In some-embodiments, cleavage of step (ii) is effected using an enzyme that cleaves RNA from an RNA/DNA hybrid. In some embodiments, the enzyme is RNaseH.

In one aspect, the invention provides methods for an aspect leading to recombining nucleic acids (making a hybrid), said methods comprising: generating a recombined nucleic acid from a hybrid nucleic acid, said hybrid molecule prepared by hybridizing a 3' single stranded portion of a complex of first and second primer extension products with a recipient nucleic acid molecule; whereby the hybrid nucleic acid is generated; wherein said complex of first and second primer extension products is prepared according to a method comprising: (i) extending a first primer hybridized to a target RNA with an enzyme comprising RNA-dependent DNA polymerase activity, wherein the first primer is a composite primer comprising an RNA portion and a 3' DNA portion, whereby a complex comprising a first primer extension product and the target RNA is produced; (ii) cleaving RNA in the complex of step (i) (cleavage may be effected, for example, with an enzyme that cleaves RNA from an RNA/DNA hybrid); (iii) extending a second primer hybridized to the first primer extension product with an enzyme comprising DNA-dependent DNA polymerase activity and RNA-dependent polymerase activity, whereby a second primer extension product is produced to form a complex of first and second primer extension products; (iv) cleaving RNA from the composite primer in the complex of step (iii) with an enzyme that cleaves RNA from an RNA/DNA hybrid such that a complex comprising hybridized first and second primer extension product comprising a 3' single stranded DNA portion is generated; (b) hybridizing the 3' single stranded portion of the complex of first and second primer extension products with a recipient nucleic acid molecule; whereby a hybrid nucleic acid is generated. In some embodiments, cleavage of step (ii) is effected using an enzyme that cleaves RNA from an RNA/DNA hybrid. In some embodiments, the enzyme is RNaseH.

In one aspect, the invention provides methods for an aspect leading to generating a complex of first and second primer extension product said complex comprising a 3' single stranded portion useful for recombining nucleic acids, said methods comprising: preparing a complex of first and second primer extension products comprising two 3' single stranded portions, wherein said complex of first and second primer extension products is prepared according to a method comprising: (i) extending a first primer hybridized to a target RNA with an enzyme comprising RNA-dependent DNA polymerase activity, wherein the first primer is a composite primer comprising an RNA portion and a 3' DNA portion, whereby a complex comprising a first primer extension product and the target RNA is produced; (ii) cleaving RNA in the complex of step (i) (cleavage may be effected, for example, with an enzyme that cleaves RNA from an RNA/DNA hybrid); (iii) extending a second primer hybridized to the first primer extension product with an enzyme comprising DNA-dependent DNA polymerase activity and RNA-dependent polymerase activity, wherein the second primer is a composite primer comprising a RNA portion and a 3' DNA portion, whereby a second primer extension product is produced to form a complex of first and second primer extension products; (iv) cleaving RNA from the composite primers in the complex of step (iii) with an enzyme that cleaves RNA from an RNA/DNA hybrid such that a complex comprising hybridized first and second primer extension product comprising two 3' single stranded DNA portion is generated. In some embodiments, cleavage of step (ii) is effected using an enzyme that cleaves RNA from an RNA/DNA hybrid. In some embodiments, the enzyme is RNaseH.

In another aspect, the invention provides methods for an aspect leading to recombining nucleic acids (making a hybrid), said methods comprising: hybridizing a 3' single stranded portion of a complex of first and second primer extension products with a recipient nucleic acid molecule, whereby a hybrid nucleic acid is generated.

In one aspect, the invention provides a method for generating a hybrid nucleic acid, said method comprising: (a) preparing a complex of first and second primer extension products said complex comprising a 3' single stranded portion, wherein said complex comprising a 3' single stranded portion is prepared according to a method comprising: (i) extending a first primer hybridized to a target RNA with an enzyme comprising RNA-dependent DNA polymerase activity, wherein the first primer is a composite primer comprising an RNA portion and a 3' DNA portion, whereby a complex comprising a first primer extension product and the target RNA is produced; (ii) cleaving RNA in the complex of step (i); (iii) extending a second primer hybridized to the first primer extension product with an enzyme comprising DNA-dependent DNA polymerase activity and an enzyme comprising RNA-dependent DNA polymerase activity, whereby a second primer extension product is produced to form a complex of first and second primer extension products; (iv) cleaving RNA from the composite primer in the complex of step (iii) with an enzyme that cleaves RNA from an RNA/DNA hybrid such that a complex comprising hybridized first and second primer extension product comprising a 3' single stranded DNA portion is generated; and (b) hybridizing the 3' single stranded portion of the complex of first and second primer extension products with a recipient nucleic acid molecule; whereby a hybrid nucleic acid is generated. As described herein, a portion or the entire 3' singled stranded portion can hybridize, as long as annealing between complex and recipient molecule occurs. In some embodiments, the methods further comprise (c) generating a recombined nucleic acid from the hybrid nucleic acid. In some embodiments, cleavage of step (ii) is effected using an enzyme that cleaves RNA from an RNA/DNA hybrid. In some embodiments, the enzyme is RNaseH.

In some embodiments of the methods described herein, the second primer comprises a fragment of the target RNA hybridized to the primer extension product, said fragment generated by cleaving RNA in the complex of step (a). Cleavage may be effected by a number of ways, including with an enzyme that cleaves RNA from an RNA/DNA hybrid, heat treatment, or chemical treatment.

In some embodiments, the methods are practiced using a composite primer in which a 5'RNA portion is adjacent to a 3' DNA portion, and making second strand is effected by using a second primer that comprises a fragment of the target RNA hybridized to the primer extension product (which was generated by RNaseH cleavage of the RNA/DNA complex resulting from extension of the composite primer).

In one aspect, the invention provides methods for recombining nucleic acids, said methods comprising: (a) preparing a complex of first and second primer extension products, said complex comprising two 3' single stranded portions, wherein said complex of first and second primer extension products is prepared according to a method comprising: (i) extending a first primer hybridized to a target RNA with an enzyme comprising RNA-dependent DNA polymerase activity, wherein the first primer is a composite primer comprising an RNA portion and a 3' DNA portion, whereby a complex comprising a first primer extension product and the target RNA is produced; (ii) cleaving RNA in the complex of step (i) (cleavage may be effected, for example, with an enzyme that cleaves RNA from an RNA/DNA hybrid); (iii) extending a second primer hybridized to the first primer extension product with an enzyme comprising DNA-dependent DNA polymerase activity and RNA-dependent DNA polymerase activity, wherein the second primer is a composite primer comprising a RNA portion and a 3' DNA portion, whereby a second primer extension product is produced to form a complex of first and second primer extension products; (iv) cleaving RNA from the composite primers in the complex of step (iii) with an enzyme that cleaves RNA from an RNA/DNA hybrid such that a complex comprising hybridized first and second primer extension product comprising two 3' single stranded DNA portion is generated; (b) hybridizing at least one 3' single stranded portion of a complex of first and second primer extension products with a recipient nucleic acid molecule; whereby a hybrid nucleic acid is generated; and (c) generating a recombined nucleic acid from the hybrid nucleic acid. In some embodiments, cleavage of step (ii) is effected using an enzyme that cleaves RNA from an RNA/DNA hybrid. In some embodiments, the enzyme is RNaseH.

In another aspect, the invention provides methods for recombining nucleic acids, said methods comprising: (a) hybridizing a 3' single stranded portion of a complex of first and second primer extension products with a recipient nucleic acid molecule, whereby a hybrid nucleic acid is generated, wherein said complex of first and second primer extension products is prepared according to a method comprising: (a) preparing a complex of first and second primer extension products comprising two 3' single stranded portions, wherein said complex of first and second primer extension products is prepared according to the following steps: (i) extending a first primer hybridized to a target RNA with an enzyme comprising RNA-dependent DNA polymerase activity, wherein the first primer is a composite primer comprising an RNA portion and a 3' DNA portion, whereby a complex comprising a first primer extension product and the target RNA is produced; (ii) cleaving RNA in the complex of step (i) (cleavage may be effected, for example, with an enzyme that cleaves RNA from an RNA/DNA hybrid); (iii) extending a second primer hybridized to the first primer extension product with an enzyme comprising DNA-dependent DNA polymerase activity and an enzyme comprising RNA-dependent DNA polymerase activity, wherein the second primer is a composite primer comprising a RNA portion and a 3' DNA portion, whereby a second primer extension product is produced to form a complex of first and second primer extension products; (iv) cleaving RNA from the composite primers in the complex of step (iii) with an enzyme that cleaves RNA from an RNA/DNA hybrid such that a complex comprising hybridized first and second primer extension product comprising two 3' single stranded DNA portions is generated; and (b) generating a recombined nucleic acid from the hybrid nucleic acid. In some embodiments, cleavage of step (ii) is effected using an enzyme that cleaves RNA from an RNA/DNA hybrid. In some embodiments, the enzyme is RNaseH.

In one aspect, the invention provides methods for recombining nucleic acids, said methods comprising: generating a recombined nucleic acid from a hybrid nucleic acid, said hybrid molecule prepared by hybridizing a 3' single stranded portion of a complex of first and second primer extension products with a recipient nucleic acid molecule; whereby the hybrid nucleic acid is generated; wherein said complex of first and second primer extension products is prepared according to a method comprising: (i) extending a first primer hybridized to a target RNA with an enzyme comprising RNA-dependent DNA polymerase activity, wherein the first primer is a composite primer comprising an RNA portion and a 3' DNA portion, whereby a complex comprising a first primer extension product and the target RNA is produced; (ii) cleaving RNA in the complex of step (i) (cleavage may be effected, for example, with an enzyme that cleaves RNA from an RNA/DNA hybrid); (iii) extending a second primer hybridized to the first primer extension product with an enzyme comprising DNA-dependent DNA polymerase activity and an enzyme comprising RNA-dependent DNA polymerase activity, wherein the second primer is a composite primer comprising a RNA portion and a 3' DNA portion, whereby a second primer extension product is produced to form a complex of first and second primer extension products; (iv) cleaving RNA from the composite primers in the complex of step (iii) with an enzyme that cleaves RNA from an RNA/DNA hybrid such that a complex comprising hybridized first and second primer extension product comprising two 3' single stranded DNA portion is generated. In some embodiments, cleavage of step (ii) is effected using an enzyme that cleaves RNA from an RNA/DNA hybrid. In some embodiments, the enzyme is RNaseH.

In another aspect, the invention provides methods for selection and/or screening recombed nucleic acids for, e.g., desired phenotype and/or encoding a protein having an advantageous predetermined property. Recombined products are useful for, e.g., methods for molecular evolution, DNA shuffling, and other methods utilizing recombined nucleic acids. Immobilized recombined products are useful, e.g., for generating microarrays.

In another aspect, the invention provides the products described herein (complexes with the 3' single stranded portion; hybrid nucleic acids; recombined nucleic acids) as made by the process(es) described herein. For example, the invention provides a hybrid nucleic acid made by a process comprising (a) preparing a complex of first and second primer extension products said complex comprising a 3' single stranded portion, wherein said complex comprising a 3' single stranded portion is prepared according to a method comprising: (i) extending a first primer hybridized to a target RNA with an enzyme comprising RNA-dependent DNA polymerase activity, wherein the first primer is a composite primer comprising an RNA portion and a 3' DNA portion, whereby a complex comprising a first primer extension product and the target RNA is produced; (ii) cleaving RNA in the complex of step (i); (iii) extending a second primer hybridized to the first primer extension product with an enzyme comprising DNA-dependent DNA polymerase activity and an enzyme comprising RNA-dependent DNA polymerase activity, whereby a second primer extension product is produced to form a complex of first and second primer extension products; (iv) cleaving RNA from the composite primer in the complex of step (iii) with an enzyme that cleaves RNA from an RNA/DNA hybrid such that a complex comprising hybridized first and second primer extension product comprising a 3' single stranded DNA portion is generated; and (b) hybridizing the 3' single stranded portion of the complex of first and second primer extension products with a recipient nucleic acid molecule; whereby a hybrid nucleic acid is generated. As described herein, a portion or the entire 3' singled stranded portion can hybridize, as long as annealing between complex and recipient molecule occurs. In some embodiments, cleavage of step (ii) is effected using an enzyme that cleaves RNA from an RNA/DNA hybrid. In some embodiments, the enzyme is RNaseH.

BRIEF DESCRIPTION OF THE DRAWINGS

FIG. 1B: shows a diagrammatic representation of a process using a composite primer and a fragment of the RNA template to generate from target RNA a complex of first and second primer extension products comprising one 3' single stranded DNA portion (overhang). The figure illustrates using an enzyme that cleaves RNA from an RNA/DNA hybrid (here, RNaseH) to effect cleavage, although other means to effect cleavage as known in the art and described herein can be used.

FIGS. 2A and B: show a diagrammatic representation of an isothermal process using two composite primers to generate from target RNA a complex of first and second primer extension products comprising two 3' single stranded DNA portions (overhangs).

FIG. 5: shows a diagrammatic representation of a method using complex of first and second primer extension products comprising a 3' overhang prepared according to methods of invention.

FIG. 6: shows a diagrammatic representation of a method using an immobilized nucleic acid and complex of first and second primer extension products comprising a 3' overhang prepared according to methods of invention.

MODES FOR CARRYING OUT THE INVENTION

Methods of the Invention

Figure 1A:
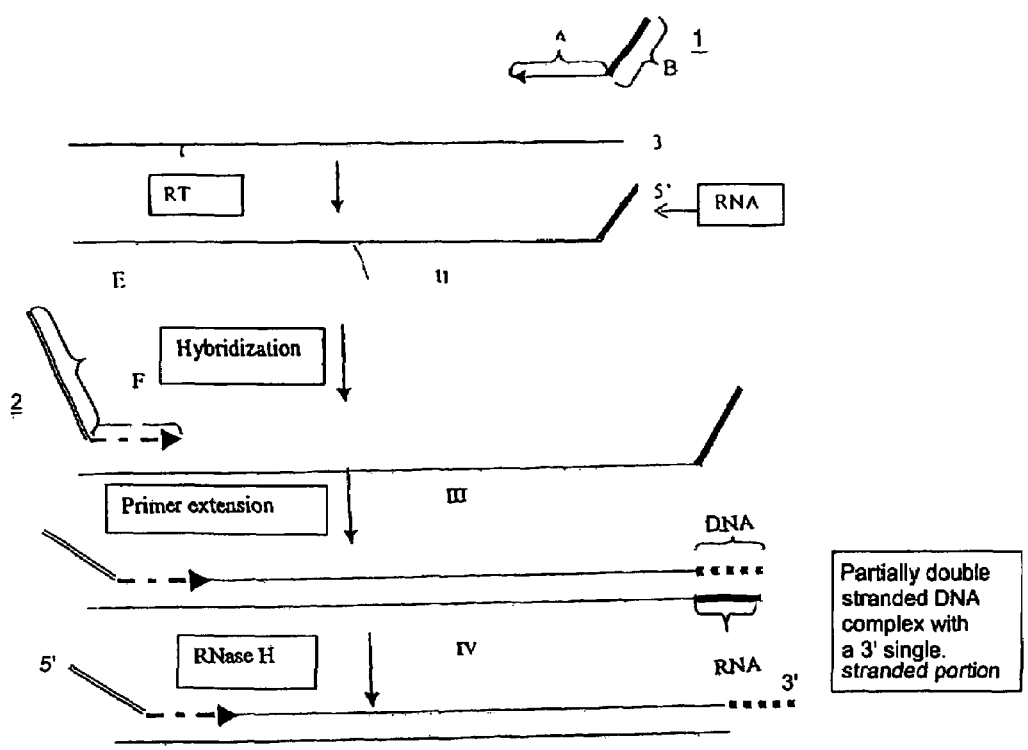
FIG. 1A: shows a diagrammatic representation of an isothermal (avoiding thermocycling) process using a composite primer and a second primer to generate from target RNA a complex of first and second primer extension products comprising one 3' single stranded DNA portion (overhang).

The methods of the invention are directed to generating hybrid nucleic acids and recombined nucleic acids using a complex with a 3' overhang (single stranded portion). The methods are convenient in that generating the complex (which arises from RNA) does not require thermocycling (e.g., PCR); as such, these methods are sometimes generally referred to being "isothermal", although the term does not indicate that any and all of the reaction temperatures must be the same (although, as described herein, for a given step, or even for a series of two or more steps, the reaction temperature may be (but need not be) the same). The methods of the invention are also directed to generating the complexes, which are useful in making hybrid and recombinant nucleic acid molecules. The methods involve generating a complex of first and second primer extension products comprising at least one 3' single stranded DNA portion (overhang), which is useful as a substrate for subsequent reactions including hybridization with a recipient molecule, whereby a hybrid nucleic acid is produced, and generation of a recombined nucleic acid (polynucleotide) from the hybrid nucleic acid.

The methods generally comprise using specially-designed primers, generally one or more RNA/DNA composite primers, to generate a partially double stranded complex of first and second strand cDNA comprising a 3' DNA single stranded end (overhang) of defined or random sequence, from RNA template. The 3' single stranded portion generally comprises the complement of an RNA portion of the composite primer. The 3' single stranded portion is the substrate for subsequent steps of the methods, such as recombination.

Generally, the complex is created as follows: a complex of first and second primer extension products comprising an RNA/DNA heteroduplex is generated from an RNA template as follows: (i) extending a first composite primer hybridized to a target RNA with an enzyme comprising RNA-dependent DNA polymerase activity, whereby a complex comprising a first primer extension product and the target RNA is produced; (ii) cleaving RNA in the complex of step (i); (iii) extending a second primer hybridized to the first primer extension product with an enzyme comprising DNA-dependent DNA polymerase activity and an enzyme comprising RNA-dependent DNA polymerase activity, whereby a second primer extension product is produced to form a complex of first and second primer extension products comprising an RNA/DNA heteroduplex at an end. An agent which cleaves RNA from an RNA/DNA hybrid (such as RNase H) cleaves RNA from the RNA/DNA hybrid, leaving a 3' single-stranded portion of the second primer extension product (an overhang) available as a substrate for further steps of the methods of the invention. In one embodiment, the second primer that primes second primer extension product synthesis is a fragment of the RNA template. As used herein, "double stranded cDNA" refers to the complex of first and second primer extension product, and "cDNA" is a polynucleotide as defined herein. Accordingly, the methods of the invention may be used for generation of a collection of partially double stranded complexes comprising sequences from a plurality of RNA sequences in the sample, each of said complexes comprising a 3' single stranded portion that is the complement of the 5' RNA portion of the composite primer.

The composite primer according to the methods of the invention comprises a 3'-DNA portion that generally is designed to be hybridizable to a target RNA(s). The sequence that is hybridizable to the RNA template defines the RNA template from which the partially double stranded complexes are generated. For example, the composite primer can comprise a poly-dT sequence, which would be expected to hybridize to the poly-A tails of all mRNA is a sample, or the composite primer can generally comprise at least a 3' portion that is hybridizable to random sequences such that the random primer portion would hybridize to random portion(s) of the template. In some embodiments, this primer further comprises a 5' portion that does not hybridize to the target mRNA under conditions which the composite primer hybridizes to the target mRNA. In another aspect, the methods of the invention may be used for generation of partially double stranded complexes from a specific RNA species or class of RNA species (e.g., a family or superfamily of RNA species). In this latter case, the composite primer generally comprises a 3'-portion which is complementary to a sequence of a specific RNA target (or family of RNA targets). In some embodiments, a portion(s) (such as a 5' RNA portion) of the composite primer can comprise a sequence that is not hybridizable (does not hybridize) to a target RNA, such as mRNA, (which would constitute a tail when the primer is bound to a target RNA) under conditions which the composit primer hbridizes to the target RNA. This non-hybridized tail is sometimes referred to as a "defined" sequence.

Target RNA can be any RNA, including translatable or untranslated RNA. RNA target may also be generated from any DNA source, including genomic DNA, using methods known in the art, including Kurn, U.S. Pat. No. 6,251,639 B1. In some embodiments, target RNA is prepared by transcription of DNA template to create the RNA complement of an DNA template (including genomic DNA and cDNA). See Kurn, U.S. Pat. No. 6,251,639 B1; Kurn, US patent publication no. 2002/0058270 A1, Thus, partially double stranded DNA comprising a 3' single stranded portion prepared according to the methods described herein can be generated from RNA copies of genomic DNA, and would thus include untranscribed sequences generally not found in mRNA, such as introns, regulatory and control elements, pseudo-genes, etc. As is evident, partially double stranded DNA comprising a 3' single stranded portion can be generated from untranslated RNA sequences, including tRNA, ribosomal RNA, small untranslated RNAs, untranslated RNA involved in disease mechanisms, and untranslated RNA that functions in gene regulation. Partially double stranded DNA comprising a 3' single stranded portion can also be generated from exogenous elements present within a genome, such as viral sequences.

As noted above, the 3' single stranded portion of the partially double stranded DNA, which is the complement of the RNA portion of the composite primer, serves as a template for further steps in the methods of the invention, for example, hybridizing at least one single stranded 3' portion of a double stranded DNA with a recipient molecule (which can be single or double stranded DNA, and can comprise a double stranded DNA comprising a single stranded 3' portion generated according to the methods of the invention described herein) whereby a hybrid nucleic acid is generated, and generation of a recombined nucleic acid from the hybrid nucleic acid. In some embodiments, the 3' single stranded portion may comprise a defined sequence (i.e., a known sequence, which is generally a sequence not hybridizable to a template nucleic acid). The hybrid molecule has a nick (created adjacent hybridized 3' end of a partially double stranded complex and 5' end of the recipient molecule, or the converse) or a gap, created as when, for example, the length of hybridizable sequence is less than the length of the 3' overhang, or when the nucleotides at the 3' end of duplex and/or 5' end of recipient molecule are not hybridized. Thus, in some embodiments, the entire 3' single stranded portion hybridizes to the recipient molecule. In other embodiments, a portion of the 3' single stranded portion (overhang) hybridizes to the recipient molecule. Thus, reference to hybridizing a singled stranded 3' portion of the complexes described herein refers to hybridization of all or a part (portion) of the single stranded 3' portion, as long as requisite annealing is accomplished. In some instances, where recombined product is produced, the extent of hybridization can be minimal, if, for example, other functions to effect recombination (joining) of nucleic acids are present (such as a polymerase and/or ligase).

The invention provides methods for recombination of hybrid polynucleotides. Recombination can be according to the methods of the invention described herein. It is also contemplated that any method known in the art can be used. Recombined polynucleotides are useful, for example, for screening and/or selecting for desirable properties, as further described herein. As used herein, and as known in this art, "recombined product" refers to a continuous (fully linked) polynucleotide comprising sequences corresponding to the partially double stranded DNA comprising a 3' single stranded portion and the recipient molecule.

Thus, one of the major advantages of the methods of the invention is the ability to create partially double stranded complexes comprising a 3' single stranded portion that include sequences from a pool of mRNAs (or other RNA targets) each connected to a defined or random 3' overhang. Depending on primer design, complexes may be generated from a specific RNA sequence of interest, or a multiplicity of RNAs, for example, members of a family of related RNAs. The methods of the invention also are suitable for generating complexes from a large multiplicity of RNAs, including all mRNA sequences in a sample. In some embodiments, double stranded complexes comprising sequences from a pool of mRNAs is generated using a single composite primer.

As noted above, the methods of the invention do not require thermocycling and all of the steps can be performed isothermally, although the various steps may be carried out at different temperatures. This feature provides numerous advantages, including facilitating automation and adaptation for high through-put procedures. The isothermal reaction is faster than that afforded by thermal cycling and is suitable for performing the methods of the invention in miniaturized devices.

As used herein, a "cDNA" or "double stranded DNA" generally is (i.e., encompasses) a polynucleotide(s). It is clear from the description herein that, although the term "polynucleotide" can refer to and include an RNA, the term "polynucleotide" is determined by the context to which it refers. For example, extension by a DNA dependent DNA polymerase generally refers to generation of a DNA molecule, but the term "DNA" is not meant (in this context, for example) to exclude molecules that contain other types of bases, analogs, linkages, etc., such as, any substrate that can be incorporated into a polymer by the polymerase Similarly, as used herein, "double stranded complexes", "DNA partial duplexes", "complex comprising a 3' single stranded portion", "double stranded DNA comprising a 3' single stranded region", "double stranded cDNA comprising a 3' overhang", and "hybridized first and second primer extension product comprising a 3' single stranded DNA portion" are used interchangeably, and refer to (encompass) polynucleotides.

General Techniques

The practice of the invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the invention can be generated using standard techniques known in the art.

Definitions

A "target sequence," "target nucleic acid," or "target RNA," as used herein, is a polynucleotide comprising a sequence of interest, for which generation of double stranded complex comprising a 3' single stranded portion is desired. The target sequence may be known or not known, in terms of its actual sequence. In some instances, the terms "target," "template," and variations thereof, are used interchangeably.

"Amplification," as used herein, generally refers to the process of producing multiple copies of a desired sequence. "Multiple copies" mean at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template, or a non-target sequence introduced through a primer), and/or sequence errors that occur during primer extension.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1–20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "labeled dNTP," or "labeled rNTP," as used herein, refers, respectively, to a dNTP or rNTP, or analogs thereof, that is directly or indirectly attached with a label. For example, a "labeled" dNTP or rNTP, may be directly labeled with, for example, a dye and/or a detectable moiety, such as a member of a specific binding pair (such as biotin-avidin). A "labeled" dNTP or rNTP, may also be indirectly labeled by its attachment to, for example, a moiety to which a label is/can be attached. A dNTP or rNTP, may comprise a moiety (for example, an amine group) to which a label may be attached following incorporation of the dNTP or rNTP into an extension product. Useful labels in the present invention include digoxigenin, fluorescent dyes (e.g., fluorescein isothiocyanate, Texas red, rhodamine, green fluorescent protein and the like), radioisotopes (e.g., $^3$H, $^{35}$S, $^{32}$P, $^{33}$P, $^{125}$I, or $^{14}$C), enzymes (e.g., LacZ, horseradish peroxidase, alkaline phosphatase) and colorimetric labels such as colloidal gold or colored glass or plastic (e.g., polystyrene, polypropylene, latex, etc.) beads. Various anti-ligands and ligands can be used (as labels themselves or as a means for attaching a label). In the case of a ligand that has a natural anti-ligand, such as biotin, thyroxine and cortisol, the ligand can be used in conjunction with labeled anti-ligands.

The "type" of dNTP or rNTP, as used herein, refers to the particular base of a nucleotide, namely adenine, cytosine, thymine, uridine, or guanine.

"Oligonucleotide," as used herein, generally refers to short, generally single stranded, generally synthetic polynucleotides that are generally, but not necessarily, less than about 200 nucleotides in length. Oligonucleotides in the invention include the composite primer. The terms "oligonucleotide" and "polynucleotide" are not mutually exclusive. The description above for polynucleotides is equally and fully applicable to oligonucleotides.

A "primer," as used herein, refers to a nucleotide sequence (a polynucleotide), generally with a free 3'-OH group, that hybridizes with a template sequence (such as a target RNA, or a primer extension product) and is capable of promoting polymerization of a polynucleotide complementary to the template. A "primer" can be, for example, an oligonucleotide. It can also be, for example, a sequence of the template (such as a primer extension product or a fragment of the template created following RNase cleavage of a template-DNA complex) that is hybridized to a sequence in the template itself (for example, as a hairpin loop), and that is capable of promoting nucleotide polymerization. Thus, a primer can be an exogenous (e.g., added) primer or an endogenous (e.g., template fragment) primer.

A "random primer," as used herein, is a primer that comprises a sequence that is designed not necessarily based on a particular or specific sequence in a sample, but rather is based on a statistical expectation (or an empirical observation) that the sequence of the random primer is hybridizable (under a given set of conditions) to one or more sequences in the sample. The sequence of a random primer (or its complement) may or may not be naturally-occurring, or may or may not be present in a pool of sequences in a sample of interest. The generation of double stranded complex from a plurality of RNA species in a single reaction mixture would generally, but not necessarily, employ a multiplicity, preferably a large multiplicity, of random primers. As is well understood in the art, a "random primer" can also refer to a primer that is a member of a population of primers (a plurality of random primers) which collectively are designed to hybridize to a desired and/or a significant number of target sequences. A random primer may hybridize at a plurality of sites on a nucleic acid sequence. The use of random primers provides a method for generating primer extension products complementary to a target polynucleotide which does not require prior knowledge of the exact sequence of the target.

A "complex" is an assembly of components. A complex may or may not be stable and may be directly or indirectly detected. For example, as is described herein, given certain components of a reaction, and the type of product(s) of the reaction, existence of a complex can be inferred. For purposes of this invention, a complex is generally an intermediate with respect to the final hybridized nucleic acid and/or recombination product(s). An example of a complex is a nucleic acid duplex comprising a first primer extension product and a second primer extension product.

A "portion" or "region," used interchangeably herein, of a polynucleotide or oligonucleotide is a contiguous sequence of 2 or more bases. In other embodiments, a region or portion is at least about any of 3, 5, 10, 15, 20, 25, 30, 35, 40, 45, 50, 60, or more contiguous nucleotides.

A region, portion, or sequence which is "adjacent" to another sequence directly abuts that region, portion, or sequence. For example, an RNA portion which is adjacent to a 5' DNA portion of a composite primer directly abuts that region. For an illustration of this example, see FIGS. 1A and 2A.

A "reaction mixture" is an assemblage of components, which, under suitable conditions, react to form a complex (which may be an intermediate) and/or a product(s).

"A", "an" and "the", and the like, unless otherwise indicated include plural forms. "A" fragment means one or more fragments.

In accordance with the well-established principle patent law, "comprising" means including.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, or strand extension, hybridization or recombining.

Sequence "mutation," as used herein, refers to any sequence alteration in a sequence of interest in comparison to a reference sequence. A reference sequence can be a wild type sequence or a sequence to which one wishes to compare a sequence of interest. A sequence mutation includes single nucleotide changes, or alterations of more than one nucleotide in a sequence, due to mechanisms such as substitution, deletion or insertion. Single nucleotide polymorphism (SNP) is also a sequence mutation as used herein. A sequence mutation can be naturally occurring in the target sequence or incorporated by in vitro manipulation of the sequence, for example, producing a copy of the sequence using a polymerase with low fidelity and other methods known in the art.

"Microarray" and "array," as used interchangeably herein, comprise a surface with an array, preferably ordered array, of putative binding (e.g., by hybridization) sites for a biochemical sample (target) which often has undetermined characteristics. In a preferred embodiment, a microarray refers to an assembly of distinct polynucleotide or oligonucleotide probes immobilized at defined positions on a substrate. Arrays are formed on substrates fabricated with materials such as paper, glass, plastic (e.g., polypropylene, nylon, polystyrene), polyacrylamide, nitrocellulose, silicon, optical fiber or any other suitable solid or semi-solid support, and configured in a planar (e.g., glass plates, silicon chips) or three-dimensional (e.g., pins, fibers, beads, particles, microtiter wells, capillaries) configuration. Probes forming the arrays may be attached to the substrate by any number of ways including (i) in situ synthesis (e.g., high-density oligonucleotide arrays) using photolithographic techniques (see, Fodor et al., *Science* (1991), 251:767–773; Pease et al., *Proc. Natl. Acad. Sci. U.S.A.* (1994), 91:5022–5026; Lockhart et al., *Nature Biotechnology* (1996), 14:1675; U.S. Pat. Nos. 5,578,832; 5,556,752; and 5,510,270); (ii) spotting/printing at medium to low-density (e.g., cDNA probes) on glass, nylon or nitrocellulose (Schena et al, *Science* (1995), 270:467–470, DeRisi et al, *Nature Genetics* (1996), 14:457–460; Shalon et al., *Genome Res.* (1996), 6:639–645;

and Schena et al., *Proc. Natl. Acad. Sci. U.S.A.* (1995), 93:10539–11286); (iii) by masking (Maskos and Southern, *Nuc. Acids. Res.* (1992), 20:1679–1684) and (iv) by dot-blotting on a nylon or nitrocellulose hybridization membrane (see, e.g., Sambrook et al., Eds., 1989, Molecular Cloning: A Laboratory Manual, 2nd ed., Vol. 1–3, Cold Spring Harbor Laboratory (Cold Spring Harbor, N.Y.)). Probes may also be noncovalently immobilized on the substrate by hybridization to anchors, by means of magnetic beads, or in a fluid phase such as in microtiter wells or capillaries. The probe molecules are generally nucleic acids such as DNA, RNA, PNA, and cDNA but may also include proteins, polypeptides, oligosaccharides, cells, tissues and any permutations thereof which can specifically bind the target molecules.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. The 3' most nucleotide(s) can be preferably from about 1 to about 50, more preferably from about 10 to about 40, even more preferably from about 20 to about 30 nucleotides.

The term "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide. The 5' most nucleotide(s) can be preferably from about 1 to about 50, more preferably from about 10 to about 40, even more preferably from about 20 to about 30 nucleotides.

As used herein, "hybrid nucleic acid molecule" refers to hybridized partially-double stranded complex and recipient molecule (which may be a second partially double-stranded complex made using the methods of the invention). A "recipient molecule" as used here is a polynucleotide to which a complex of first and second primer extension product comprising at least one 3' overhang hybridizes.

As used herein "recombined product" refers to a continuous (fully linked) polynucleotide comprising sequences corresponding to the partially double stranded complex comprising a 3' single stranded portion and the recipient molecule. A recombined product can, but does not necessarily, comprise all sequences corresponding to the partially double stranded complex comprising a 3' single stranded portion and the recipient molecule, as some of the methods for generating recombined product described herein result in deletion and/or mutation of sequences corresponding to the original partially double stranded complex (comprising a 3' overhang) and recipient molecule. "Recombining nucleic acids" refers to generating a recombined product. This can be accomplished in any of a number of ways (including ligation) as described herein.

Methods of the Invention Using Partially Double Stranded Complexes Comprising a 3' Overhang The following are examples of the methods of the invention. It is understood that various other embodiments may be practiced, given the general description provided above. For example, reference to using a composite primer means that any of the composite primers described herein may be used.

The methods of the invention involve production of a complex comprising a partially double stranded complex comprising a 3' DNA single stranded portion (overhang) of defined or random sequence, from an RNA template. The 3' single stranded end of the complex (all or part) is hybridizable to a 3' single stranded portion of a second nucleic acid, termed a recipient nucleic acid which may be single stranded or a second partially double stranded complex comprising a 3' single stranded portion (which can be a second partial double stranded complex comprising a 3' single stranded overhang according to the methods of the invention described herein). Hybridization of the 3' single stranded portions of the complex and the second nucleic acid generates a hybrid (annealed) nucleic acid. A recombined nucleic acid (which can be immobilized to a surface) is generated from the hybrid nucleic acid by any of a number of methods, as known in the art and described herein.

Uses of recombined products are known in the art and include subsequent screening and/or selection of recombined products, and further uses described herein. These uses are encompassed by the invention.

For simplicity, the methods for production of the partially double stranded complex comprising a 3' single stranded portion (overhang) are described separately from the methods for production of hybrid nucleic acids and generation of recombined product. It is understood that each method for production of the complex is applicable to each method for production of a hybrid nucleic acid and/or generation of recombined product, and vice versa.

Formation of a Complex Comprising a Partially Double Stranded Complex Comprising a 3' Single Stranded Sequence FIG. 1A illustrates a schematic description of one embodiment of the methods for formation of partially double stranded DNA comprising a 3' single stranded DNA sequence from an RNA template. The methods involve the following steps: (a) formation of a double stranded cDNA comprising a RNA-DNA heteroduplex at one end as follows: (i) extending a first composite primer hybridized to a target RNA with an enzyme comprising RNA-dependent DNA polymerase activity, whereby a complex comprising a first primer extension product and the target RNA is produced; (ii) cleaving RNA in the complex of step (i); (iii) extending a second primer hybridized to the first primer extension product with an enzyme comprising DNA-dependent DNA polymerase activity and an enzyme comprising RNA-dependent DNA polymerase activity, whereby a second primer extension product is produced to form a complex of first and second primer extension products comprising an RNA/DNA heteroduplex at an end and (b) cleavage of RNA in the RNA-DNA heteroduplex to generate a partially double stranded DNA comprising a 3' single stranded DNA portion (interchangeably termed "overhang"). As illustrated, all steps are isothermal, although the temperatures for each of the steps may or may not be the same. The methods of the invention do not require thermal cycling (i.e., PCR), and the complex of template RNA and first primer extension product is not denatured or separated using thermal denaturation.

The embodiment illustrated in FIG. 1A employs two oligonucleotides: a composite primer, (labeled 1); and a second primer (labeled 2), used for the formation of the second primer extension product (interchangeably called "second strand cDNA").

As illustrated in these figures, the composite primer 1 comprises a DNA portion, A, at its 3' end, and an RNA portion, B, at its 5' end. As discussed herein, it is also possible to employ a composite primer in which the 3' DNA portion is followed, in the direction of its 5', by an RNA portion, which is followed by a portion which is DNA. The length of each of these sections is generally determined for maximum efficiency of the formation of the partially double stranded complexes comprising a 3' single stranded DNA sequence, and the subsequence recombination mediated by the 3' single stranded end. Only the two-portion (i.e., 3'-DNA-RNA-5') composite primer is shown in FIGS. 1A, 1B and FIGS. 2A–B.

The 5' portion of the composite primer may or may not be hybridizable to target sequence. In some embodiments, the 5' portion of composite primer 1 as illustrated in FIGS. 1A and B, and 2A comprises a sequence not hybridizable to the target sequence, e.g., a sequence forming a "tail" when the primer is hybridized to a target. The 5' portion generally is incorporated into the first primer extension product (first strand cDNA), and the 3' overhang (single stranded DNA portion) of the complex of double stranded DNA comprises the complement of the 5' portion of the composite primer. As described herein, the single stranded DNA portion is the substrate for subsequence hybridization and recombination. In another embodiment, the 5' portion of the first primer is hybridizable to the target RNA. The 5' portion of the first primer can be designed in any of a number of ways (in terms of sequence) depending on which type, class, population, and/or species of recombination is desired between the complex and the second nucleic acid. As noted above, length and sequence of the overhang in the resultant partial double stranded DNA complex is determined by the length and sequence of the RNA portion of the composite primer that binds to target RNA. The length is generally at least two ribonucleotides, although as discussed below, longer RNA portions are contemplated by the invention.

The sequence of the 5' portion can be known (termed a "defined sequence"), and in some embodiments, comprises a restriction site. The defined sequence can be selected to be hybridizable to a known sequence or a family of known sequences (for example, a kinase domain). In some embodiments, the 5' defined sequence can be a unique sequence, in the sense that the sequence is not expected to be hybridizable to template RNA. In other embodiments, the 5' portion is a random sequence. In still other embodiments, the 5' portion comprises a defined sequence and a random sequence. The sequence of the RNA portion can be selected to, for example, comprise sequences corresponding to (the complement of which are hybridizable to) a 3' single stranded overhang generated by restriction digest of double stranded DNA, thus permitting hybridization of the complex to a recipient molecule cut with the restriction enzyme. As used herein, sequences that "correspond" to a 3' single stranded are sequences that are generally hybridizable to the complement of the 3' single stranded overhang sequence.

The 3' overhang can also be selected to hybridize with recipient molecules (interchangeably called "recipient nucleic acids") comprising a defined 3' overhang region. The defined region may be a unique sequence, such that hybridization occurs generally with recipient molecules comprising the same unique sequence. Alternatively, the defined sequence can correspond to a sequence hybridizable to a sequence present in 3' end of recipient molecule, or a family or related recipient molecules (e.g., gene family or superfamily). In another embodiment, the 3' overhang is random, so that the complexity of the hybridization step is greatly increased (in terms of number of potentially hybridizable recipient molecules, for example).

The 3' overhangs can also be selected to generate recombination products with insertions of varying lengths (corresponding to sequences contained in the 3' overhangs). For example, if a partially double stranded complex comprising a 3' overhang is hybridized to a recipient molecule comprising a 3' unique sequence (in the sense that it is not a sequence present in target RNA, but rather constitutes an appended 3' sequence), nucleotides corresponding to the unique sequence will be inserted into the recombination product. In another example, if the 3' overhang corresponds to a random sequence in the first composite primer, generally the recombination product comprises nucleotides hybridizable to the random sequence.

However, if either 3' end is generated from a sequence present in the target RNA, hybridization generates a double stranded portion corresponding to target RNA, and new nucleotides are generally not inserted in the final recombined product.

It is understood that the 3' ends of the partially double stranded complex and recipient need not hybridize with perfect complementarity, depending on the level of stringency used during the hybridization of complex and recipient molecule. Selection of suitable hybridization conditions is described further herein. It is appreciated that use of reduced stringency increases the number of 3' overhangs which will tend to hybridize with one another.

In addition, the 3' ends of the partially double stranded complex and recipient molecules need not be of the same length. One or more gaps can be present after hybridization, which may be filled using a variety of methods described herein.

3' ends may also be selected such that hybridization between partially double stranded complex and recipient molecule is directional. For example, a population of partially double stranded complex molecules and a second population of recipient molecules (which may also be partially double stranded complex molecules) may be generated such that hybridization is in a particular, specified orientation with respect to each other.

As noted above, the use of 3' ends corresponding to random 5' RNA portions would be expected to permit hybridization in all orientations (and thus to increase the complexity of recombination).

Further, the sequence of the 3' end may be selected such that hybridization is favored or disfavored, for example, increasing GC content of the 3' end, and using nucleotide analogs (including PNA) known to increase or decrease capacity to hybridize, as well as other factors known in the art.

The 3' portion of the first composite primer (which hybridizes to template RNA) can be designed in any of a number of ways (in terms of sequence), depending on which type, class, population, and/or species of RNA is desired to be incorporated into the partially double stranded DNA complex (that comprises a 3' single stranded region). In some embodiments, the 3' portion of composite primer 1 illustrated in FIGS. 1 and 2 comprises a sequence complementary to the poly-A tail of mRNA, and may further comprise additional random sequences (generally not complementary to a poly-A sequence) at the 3' end of the 3' portion. In other embodiments, the 3' portion of composite primer 1 is a random primer comprising sequences which are hybridizable to a multiplicity, a large multiplicity or a very large multiplicity of RNA species. Random primers are known in the art, for example, they have been used extensively in the preparation of cDNA libraries using PCR-based procedures. As is well understood in the art, a "random primer" can refer to a primer that is a member of a population of primers (a plurality of random primers) which collectively are designed to hybridize to a desired and/or a significant number of target sequences. A random primer may hybridize at a plurality of sites on a nucleic acid sequence. In other embodiments, the 3' portion of composite primer 1 can comprise a sequence hybridizable to a specific RNA or family of RNAs (or portions thereof).

In some embodiments, composite primer 1 is a mixture of different composite primers which comprise the same 5' RNA portion and a multiplicity of 3' DNA portions selected to amplify a multiplicity of RNA sequences of interest (which may range from 2 or more to many hundred or thousands or more).

The second primer is any sequence that is hybridizable to the first DNA strand such that it is capable of being extended by a DNA polymerase along a first primer extension product to create a second primer extension product. Primer 2 as illustrated in FIGS. 1A–B can be, but is not necessarily, composed of DNA and can comprise two sections (interchangeably called "portions" or "regions"). The 3' portion, F, of primer 2 can be selected for random priming of many, most and/or all possible mRNA sequences in a biological sample. The 5' portion, E, of primer 2 can be a sequence which is not complementary and not substantially hybridizable to a specific target sequence, i.e., it would not hybridize and would constitute a tail. The "tail" sequence would generally be incorporated into the second primer extension product. In other embodiments, the 5' end portion, E, of primer 2 can be hybridizable to the target sequence in the first primer extension product. In still other embodiments, it comprises a sequence of the first DNA strand (generally at the 3' end) that is hybridized to a sequence in the first DNA strand (for example, a hairpin or self-annealed structure).

In one embodiment, a fragment of the target RNA serves as the primer of the second primer extension product. This embodiment of the invention is illustrated in FIG. 1B, and discussed further below. The target RNA in the initial complex comprising the target RNA and first primer extension product is cleaved such that at least one fragment of the template RNA remains hybridized to the first primer extension product. In some embodiments, the cleavage is effected using an agent such as an enzyme that effects cleavage of RNA from an RNA/DNA hybrid, such as RNaseH. In this aspect of the invention, one (or more) template RNA fragment(s) serves as a second "primer" in the manner described above, to generate a fragment extension product which has the same function as the second primer extension product in the methods described above. A suitable RNA fragment in the methods of the invention is long enough such that it does not dissociate from the first strand cDNA, preferably from about 3 to about 30, more preferably from about 5 to about 25, even more preferably from about 10 to about 20, and most preferably from about 12 to about 17, nucleotides in length. Template RNA can be cleaved using methods well-known in the art, including cleavage with an enzyme (such as RNAse H) that cleaves RNA from an RNA-DNA hybrid, cleavage resulting from heat treatment, and cleavage due to chemical treatment (e.g., treatment under alkaline conditions). As used herein, template cleavage does not encompass separation of template RNA and first primer extension using of heat that is sufficient to separate or denature template RNA from first primer extension product (for example, by using thermal cycler or other means of temperature controlled inclubation).

As illustrated in FIG. 1A, in one embodiment, the process of the methods of the invention resulting in formation of partially double stranded complexes comprising a 3' single stranded DNA sequence from an RNA template is as follows:

1. Primer 1 binds to an RNA species in a sample by hybridization of the random sequence portion A (which can be based at least in part on the poly-A sequence of the mRNA), to form complex I (FIG. 1A).
2. A reverse transcriptase, (indicated as "RT"), extends the hybridized primer 1 along the target RNA strand to which it is hybridized, to form an RNA/DNA duplex. An agent (such as RNase H) degrades the target RNA strand of the hybrid duplex to generate a single stranded first strand cDNA (labeled "II"). The 5' end of II is primer 1.
3. Primer 2 binds to the first strand cDNA, II, by hybridization of the random sequence F, to form complex III.
4. Primer 2 is extended along the first cDNA strand II by a DNA polymerase to form a double stranded product (labeled "IV"). Primer extension along the 5' RNA portion of II by an RNA-dependent DNA polymerase such as a reverse transcriptase results in formation of an RNA/DNA hybrid portion at one end of complex IV. DNA-dependent polymerase activity and RNA-dependent polymerase activity can be provided in the same enzyme.

RNase H degrades the RNA portion of the RNA/DNA hybrid at one end of complex IV, to create a partial double stranded complex (labeled "V") with a 3' DNA single stranded end, which has a sequence which is the complement of portion B of the composite primer 1. The RNase H activity may be supplied by the RNA-dependent DNA polymerase (such as reverse transcriptase) or may be provided in a separate enzyme. Reverse transcriptases useful for this method may or may not have RNase H activity. The DNA dependent DNA polymerase used for the second primer extension step may supply the reverse transcriptase activity for replication of the 5' RNA portion of the first primer extension product, or a second enzyme may provide it.

FIG. 1B illustrates an embodiment of the invention wherein a fragment of the target RNA serves as the primer of the second primer extension product. As illustrated in FIG. 1B, the single (composite) primer (labeled "I") can be composed of a 3'-DNA portion (labeled "A") which is complementary to a sequence on the target RNA, and a 5'-RNA portion (labeled "B") which comprises a non-target related sequence (i.e., it is not complementary or hybridizable under a given set of conditions to a sequence on the target RNA under which "A" does hybridize). The 3'-DNA portion of the composite primer may comprise poly-dT nucleotides, which would render it complementary/hybridizable (under a given set of conditions) to the poly-A 3' end of mRNA derived from a eukaryotic cell.

1. Composite primer 1 that is hybridized to a target RNA (complex "I" in FIG. 1B) is extended by an RNA-dependent DNA polymerase, such as a reverse transcriptase, to form an RNA/DNA heteroduplex of the target RNA and a first strand cDNA (complex "II" in FIG. 1B).
2. Target RNA is then degraded (fragmented), for example, by use of a ribonuclease such as RNase H, to form a complex of the first strand cDNA and one or more RNA fragments (oligonucleotides) (complex "III" in FIG. 1B). The fragments are a result of incomplete degradation of the target RNA in the heteroduplex.
3. These fragments function as primers for a DNA-dependent DNA polymerase to form the second strand cDNA. Okayama & Berg, *Molecular and Cell Biology* (1982), 2:161–170; and Gubler & Hoffman, *Gene* (1983), 25:263–269. An RNA-dependent DNA polymerase (such as reverse transcriptase) then extends the 3'-end of the second strand cDNA in the duplex along the 5'-RNA sequence of the composite primer extension product (the first strand cDNA), to form an RNA/DNA heteroduplex at the end of the double stranded cDNA product (complex "IV" in FIG. 1B).
4. The heteroduplex at the end of the double stranded cDNA is a substrate for RNase H. RNase H degrades the RNA portion of the RNA/DNA hybrid at one end of complex IV, to create a partial double stranded complex (labeled "V") with a 3' DNA single stranded end, which has a sequence which is the complement of portion B of the composite primer 1.

The methods of the invention may be used for generation of a "library" of partially double stranded complexes comprising sequences from a plurality of RNA sequences in the sample. For example, the composite primer can comprise a poly-dT sequence, which would be expected to hybridize to the poly-A tails of all mRNA is a sample, or the composite primer can generally comprise at least a 3' portion that is hybridizable to random sequences such that the random primer portion would hybridize to random portion(s) of the template. In another aspect, the methods of the invention may be used for generation of partially double stranded complexes from a specific RNA species or class of RNA species (e.g., a family or superfamily of RNA species). In this latter case, the composite primer generally comprises a 3'-portion which is complementary to a sequence of a specific RNA target (or family of RNA targets).

For convenience, only one first primer extension product (first strand cDNA) and second strand primer extension product (second strand cDNA) are described and illustrated in FIGS. 1A, 1B, and 2. It is to be understood that the methods of the invention are useful not only for generating partially double stranded complexes comprising double stranded copies of one RNA sequence, but also for generating complexes simultaneously from more than one different specific nucleic acid sequence located on the same or different targetRNA molecules.

As described herein, partially double stranded complexes can be generated from RNA target that is itself generated from a DNA source (such as genomic DNA), using methods known in the art, including Kurn, U.S. Pat. No. 6,251,639. Thus, partially double stranded complexes prepared according to the methods described herein can correspond to RNA copies of genomic DNA, and would thus include untranscribed sequences generally not found in mRNA, such as introns, regulatory and control elements, etc. As is evident, partially double stranded DNA comprising a 3' single stranded portion can be generated from untranslated RNA sequences, including tRNA, ribosomal RNA, small untranslated RNAs, untranslated RNA involved in disease mechanisms, and untranslated RNA that functions in gene regulation.

Formation of a Complex Comprising a Partially Double Stranded DNA Comprising Two 3' Single Stranded Sequences A schematic description of one embodiment of the formation of partially double stranded DNA comprising two 3' single stranded DNA sequences from an RNA template is given in FIG. 2A and B. The methods involve (a) formation of a double stranded cDNA comprising a RNA-DNA heteroduplex at each end of the cDNA as follows: (i) extending a first composite primer hybridized to a target RNA with an enzyme comprising RNA-dependent DNA polymerase activity, whereby a complex comprising a first primer extension product and the target RNA is produced (ii) cleaving RNA in the complex of step (i); (iii) extending a second composite primer hybridized to the first primer extension product with an enzyme comprising DNA-dependent DNA polymerase activity and an enzyme comprising RNA-dependent DNA polymerase activity, whereby a second primer extension product is produced to form a complex of first and second primer extension products comprising an RNA/DNA heteroduplex at each end and (b) cleavage of RNA in the RNA-DNA heteroduplexes to generate a partially double stranded complex comprising two 3' single stranded DNA portions (or overhangs). As illustrated, all steps are isothermal, although the temperatures for each of the steps may or may not be the same. As is evident, in this aspect of the invention, production of the second strand cDNA is primed using another composite primer capable of hybridizing to the first strand cDNA. As used herein, the term "cDNA" refers to first and second primer extension product comprising polynucleotides.

The embodiment illustrated in FIGS. 2A–B employs two oligonucleotides: a first composite primer, (labeled 1) used for the formation of the first primer extension product; and a second composite primer (labeled 2), used for the formation of the second primer extension product. The 5' portion of the first composite primer is generally incorporated into the first primer extension product, and the 5' portion of the second (reverse) composite primer generally is incorporated into the second primer extension product (second strand cDNA). The complements of the 5' portion of the first and second composite primer comprise each of the two 3' single stranded portions of the complex of double stranded DNA.

In FIG. 2A and B, two composite primers comprising "tail" sequences are used to generate a double stranded cDNA comprising a RNA-DNA heteroduplex at each end of the cDNA. Cleavage of RNA by an agent that cleaves RNA from an RNA/DNA heteroduplex creates a partially double stranded complex with two 3' DNA single stranded ends.

The 5' portion of composite primer 2 as illustrated in FIG. 2A can comprise a sequence not hybridizable to the target sequence or to the first primer extension product, e.g., a sequence forming a "tail" when the primer is hybridized to the first primer extension product. In some embodiments, this 5' portion is a "defined" sequence or, in some embodiments, is a random sequence. The 5' portion of composite primer 2 can be the same as or different than the 5' portion of composite primer 1.

The process of the methods of the invention resulting in formation of partially double stranded complex comprising two 3' single stranded DNA portions from an RNA template is as follows:
1. Composite primer 1 binds to an RNA species in a sample by hybridization of sequence portion A (which can be based at least in part on the poly-A sequence of the mRNA), to form complex I. Composite primer 1 can, but does not necessarily, comprise a "tail" sequence (depicted as a thick black line) that is not hybridizable to the template mRNA.
2. A reverse transcriptase extends the hybridized primer 1 along the target RNA strand to which it is hybridized, to form an RNA/DNA duplex, labeled II. An agent (such as RNase H) degrades the target RNA strand of the hybrid duplex to generate a single stranded cDNA (labeled "III"). The 5' end of III is primer 1.
3. Composite primer 2 binds to the first strand cDNA, III, by hybridization of sequence F, to form complex IV. The reverse composite primer further comprises a "tail" sequence (depicted as a thick dotted line) that is not hybridizable to the template RNA or the first strand cDNA. The tail sequences of composite primer 1 and the second composite primer can be different sequences, although in some embodiments, the tail sequences can be the same sequence.
4. The composite primer 2 is extended along the first strand cDNA III by a DNA polymerase to form a double stranded product (labeled "V"). Primer extension along the 5' RNA portion of IV by an RNA-dependent DNA polymerase such as a reverse transcriptase results in formation of an RNA/DNA hybrid portion at one end of complex V. DNA-dependent polymerase activity and RNA-dependent polymerase activity can be provided in the same enzyme, as described herein.
5. An agent (such as RNase H) degrades the RNA portion of the RNA/DNA hybrid at one end of complex V, to create a partial double stranded complex (labeled "VI") with a 3' DNA single stranded end, which has a sequence which is the complement of portion B of the composite primer 1.
6. Composite primer 1 binds to complex VI by hybridization of the RNA portion to the single stranded DNA end, which is complementary to it, to form complex VII
7. Primer extension of bound primer 1 in complex VII along the sense cDNA strand results in displacement of the previous cDNA product (VII), and replicates the tail sequence of the second composite primer, to form complex VIII.
8. Complex VIII has two RNA/DNA heteroduplexes comprised of composite primer 1 and the complement of composite primer 1 at one end, and composite primer 2 and the complement of the composite primer 2 at the other end. An agent (such as RNase H) cleaves the RNA portions of the RNA/DNA heteroduplexes, forming a partially double stranded DNA comprising two 3' single stranded DNA sequences. The RNase H activity may be supplied by the enzyme comprising RNA-dependent DNA polymerase activity (such as reverse transcriptase) or may be provided in a separate enzyme. Reverse transcriptases useful for this method may or may not have RNase H activity. One 3' DNA single stranded end has a sequence which is the complement of portion B of the composite primer 1, and one 3' DNA single stranded end has a sequence which is the complement of portion B of composite primer 2.

Design of the composite primers of these embodiments of the invention is generally governed by the same consideration described above for the methods of generating a partially double stranded complex with a single 3' end. However, it is understood that the composite primer that binds to target RNA and the composite primer that binds to first primer extension product generally have different 5' RNA portions. The 5' RNA portions can be selected such that the resultant 3' overhangs are mutually hybridizable (e.g., by designing hybridizable sequences or using random sequence in one or both 5' portion), or designed such that the 3' overhangs are hybridizable with one or more recipient molecules.

Methods Using the Partially Double Stranded Complex Comprising a 3' Single Stranded Portion The invention provides methods for aspects of recombining nucleic acids. In some embodiments, the methods comprise hybridizing a 3' single stranded portion of a partially double stranded DNA with a recipient nucleic acid molecule whereby a hybrid nucleic acid is generated; said partially double stranded complex comprising a 3' single stranded portion prepared according to any of the methods described herein. In another aspect, the invention provides methods for recombining nucleic acids comprising: hybridizing a 3' single stranded portion of a partially double stranded complex with a recipient nucleic acid molecule whereby a hybrid nucleic acid is generated (as noted above and herein, all or a part (portion) of the 3' single stranded portion can hybridize); said partially double stranded complex comprising a 3' single stranded portion prepared according to any of the methods described herein, and generating a recombined nucleic acid from the hybrid nucleic acid. As used herein "recombined product" refers to a continuous (fully linked) polynucleotide comprising sequences corresponding to the partially double stranded DNA comprising a 3' single stranded portion and the recipient molecule. A recombined product can, but does not necessarily, comprise all sequences corresponding to the partially double stranded DNA comprising a 3' single stranded portion and the recipient molecule, as some of the methods for generating recombined product described herein result in deletion and/or mutation of sequences corresponding to the original partially double stranded DNA (comprising a 3' overhang) and/or recipient molecule. As used herein, a "cDNA" or "partially double stranded DNA" or "double stranded DNA" is (i.e., encompasses) a polynucleotide(s). As noted above, it is clear from the description herein that, although the term "polynucleotide" can refer to and include an RNA, the term "polynucleotide" is determined by the context to which it refers. For example, extension by a DNA dependent DNA polymerase generally refers to generation of a DNA molecule, but the term "DNA" is not meant (in this context, for example) to exclude molecules that contain other types of bases, analogs, linkages, etc., such as, any substrate that can be incorporated into a polymer by the polymerase Methods for producing a hybrid nucleic acid The partially double stranded DNA comprising a 3' single stranded portion (interchangeably called "partially double stranded complex") is prepared according to any of the methods of the invention described herein. The partially double stranded complex can comprise a single 3' overhang or two 3' overhangs (one at each end). It is understood that partially double stranded complexes of the invention can be a multiplicity (from few to very many) of different partially double stranded complexes (corresponding to a multiplicity of target RNAs) generated according to any of the methods described herein. Methods and approaches for generating populations of different partially double stranded complexes are described herein. Such populations can be related in sequence (e.g., member of a gene family, comprising sequence corresponding to a certain motif or domain) or extremely diverse in sequence (e.g., generated from all mRNA using a poly-dT or random composite primer; generated from all RNA in a target population using a random primer). As described herein, partially double stranded complexes can be generated from RNA target that is itself generated from a DNA source (such as genomic DNA), using methods known in the art, including Kurn, U.S. Pat. No. 6,251,639 B1. Thus, partially double stranded complexes prepared according to the methods described herein can be generated from RNA copies of genomic DNA, and would thus include untranscribed sequences generally not found in mRNA, such as introns, regulatory and control elements, etc.

A recipient molecule can (interchangeably called "recipient molecule" or "recipient") be partially double stranded comprising one or two 3' single stranded portions (3' overhangs). Double stranded recipient molecule can be a second partially double stranded polynucleotide (such as DNA) comprising one or two 3' single stranded portion(s) prepared according to any of the methods of the invention described herein. Other sources for partially double stranded recipient (comprising one or two 3' overhangs) include at least the following: double stranded cDNA, double stranded genomic DNA (from one or more genomic source), double stranded DNA prepared from a library, and double stranded DNA prepared using any method known in the art, including PCR (see, e.g., Jarrell WO 00/40715). Methods for generating partially double stranded DNA comprising one or two 3' (single stranded) overhangs are known in the art and include restriction digestion with a suitable restriction enzyme, Dnase digestion, mechanical shearing of double stranded DNA, and additional methods described in, for example, U.S. Pat. Nos. 6,344,356; 6,319,714.

The recipient nucleic acid molecule can be single stranded. In some embodiments, the single stranded recipient is immobilized on a surface (as further described below). Single stranded recipient may be prepared from at least the following sources: single stranded DNA prepared using any method known in the art, including methods described in Kurn, U.S. Pat. No. 6,251,639; Kurn, U.S. Patent Publication No. 2002/0058270; Kurn, co-pending U.S. patent application No. 10/100,321; first strand cDNA prepared using method known in the art; as well as from any double stranded DNA or DNA/RNA hybrid molecule simply by rendering the DNA single stranded using methods well known in the art.

It is understood that a recipient molecule can be a multiplicity (from small to very large) of different recipient molecules. Such populations can be related in sequence (e.g., member of a gene family; comprising sequence corresponding to a certain motif or domain) or extremely diverse in sequence (e.g., generated from all mRNA, generated from a population of genomic DNA, etc.). Alternatively, recipient molecules can correspond to single sequence (which can be part or all of a known gene, for example a coding region, genomic portion, etc.)

Recipient molecules can be selected from one or more sources described herein. For example, recipient molecules can include recipient molecules that are partially double stranded DNA comprising a 3' overhang prepared according to methods described herein and other single stranded and/or double stranded recipient molecules.

Moreover, it is understood that partially double stranded complexes (comprising 3' overhang) and/or recipient molecules may correspond to RNA or DNA from one or a multiplicity (which can be small to very large) of organisms, and may be native or non-native (e.g., mutated, synthetic, etc.) DNA or RNA. Thus, the notion of a "gene family" (or related nucleic acid sequences) as used herein encompasses both related sequences from a particular organisms as well as sequences related across a multiplicity of organisms.

Partially double stranded complexes and/or recipient molecules can be selected in any of a number of ways depending on which type, class, population, and/or species of nucleic acid is desired to be incorporated into a hybrid molecule (i.e., following hybridization of 3' ends of a partially double stranded complex and a recipient molecule). For example, nucleic acid corresponding to a particular protein, protein domain, protein subdomain, protein motif, protein family or superfamily, etc. may be selected. In an additional example, nucleic acid corresponding to an exon, open reading frame, exon-intron region, and/or untranslated region (or any combination thereof) may also be selected. In another example, nucleic acids may correspond to randomly generated nucleic acids. In yet another example, nucleic acid can correspond to untranslated RNA sequences. These examples are further discussed herein.

Methods for selecting type, class, population, and/or species of partially double stranded DNA comprising a 3' overhang are described herein. Generally, the 3' portion of the first composite primer is designed in any of a number of ways (in terms of sequence), depending on which type, class, population, and/or species of RNA is desired to be incorporate into the partially double stranded complex (that comprises a 3' single stranded region), as discussed herein.

Methods for selecting type, class, population and/or species of recipient molecule are well known in the art, and include: amplification of desired sequence(s) using PCR; restriction endonuclease digestion of DNA, including genomic DNA; preparation of previously cloned DNA; and other well known methods in the art. It is understood that recipient molecules may be prepared from a variety of sources including: RNA, DNA, RNA/DNA hybrids; single stranded DNA; double stranded DNA, etc.

The following discussion describes certain exemplary nucleic acids which may be represented in a partially double stranded complex comprising a 3' overhang (prepared according to methods of the invention) and/or recipient molecule. It is understood that partially double stranded complexes and recipient molecules may comprise one or more of the features described below.

In some embodiments, partially double stranded complexes and/or recipient molecules correspond to open reading frames (or partial open reading frames). In other embodiments, partially double stranded complexes and/or recipient molecules correspond to genomic DNA (and thus may comprise exon, intron and/or untranslated regions, etc.). In other embodiments, partially double stranded complexes and/or recipient molecules correspond to randomly selected/generated portions.

In some embodiments, partially double stranded complexes and/or recipient molecules correspond to known sequences or groups of related sequences. For example, partially double stranded complexes and/or recipient molecules can correspond to one or more discrete full-length or partial functional domains of known biological activity. It is well known in the art that many proteins have discrete functional domains (see, for example, Traut, *Mol. Cell. Biochem.* 70:3 (1986); Go, *Adv. Biophys.* 19:91 (1985)). It is also well known that such domains may often be separated from one another and recombined with other discrete functional domains in a manner that preserves the activity of each individual functional domain.

Examplary functional protein domains include, for example, DNA binding domains (such as zinc fingers, homeodomains, helix-turn-helix motifs, etc.), ATP or GTP binding domains, transmembrane spanning domains, protein-protein interaction domains (such as leucine zippers, TPR repeats, WD repeats STYX domains (see, for example, Wishart et al., *Trends Biochem. Sci.* 23: 301, 1998), G-protein domains, tyrosine kinase domains (see, for example, Shokat, *Chem. Biol.* 2:509, 1995), SRC homology domains (see, for example, Sudol, *Oncogene* 17:1469, 1998), SH2 domains (see, for example, Schaffhausen, *Biochim. Biophys. Acta* 28:61, 1995), PTB domains (see, for example, van der Greer et al., *Trends Biochem. Sci.* 20:277, 1995), the PH domain (see, for example, Musacchio et al., *Trends Biochem. Sci.* 18:343, 1993), certain catalytic domains and cell surface receptor domains (see, for example, Campbell et al., *Immunol. Rev.* 163:11, 1998), carbohydrate recognition domains (see, for example, Kishore et al., *Matrix Biol* 15:583, 1997), immunoglobulin domains (see, for example, Rapley, *Mol. Biotechnol.* 3:139, 1995).

Functional protein domains suitable for use in accordance with the present invention include those that have been reused through evolution to generate gene families. Examples of such gene families include, for example, the tissue plasminogen activator gene family (see, for example, WO 00/40715, FIG. 6), the family of voltage-gated sodium channels (see, for example, Marban et al., *J. Physiol.* 508: 647, 1998), certain families of adhesion molecules (see, for example, Taylor et al., *Curr. Top. Microbiol. Immunol.* 228:135, 1998), various extracellular domain protein families (see, for example, Engle, *Matrix Biol* 15:295, 1996), the protein kinase C family (see, for example, Dekker et al., *Curr. Op. Struct. Biol.* 5:396, 1995), the tumor necrosis factor receptor superfamily (see, for example, Naismith et al., *J. Inflamm.* 47:1, 1995), the lysin family (see, for example, Lopez et al., *Microb. Drug Resist* 3:199, 1997), the nuclear hormone receptor gene superfamily (see, for example, Ribeiro et al., *Annu. Rev. Med.* 46:443, 1995; Carson-Jurica et al., *Endocr. Rev.* 11:201, 1990), the neurexin family (see, for example, Missler et al., *J. Neurochem.* 71:1339, 1998), the thioredoxin gene family (see, for example, Sahrawy et al., *J. Mol. Evol.* 42:422, 1996), the phosphoryl transfer protein family (see, for example, Reizer et al., *Curr. Op. Struct. Biol.* 7:407, 1997), the cell wall hydrolase family (see, for example, Hazelwood et al., *Prog. Nuc. Acid Res. Mol. Biol.* 61:211, 1998), and certain families of synthetic proteins (e.g., fatty acid synthases, polyketide synthases (see, for example, WO 98/01546, U.S. Pat. No. 5,252,474, U.S. Pat. No. 5,098,83), peptide synthetases (see, for example, Mootz et al., *Curr. Op. Chem. Biol.* 1:543, 1997; Stachelhaus et al., *FEMS Microbiol. Lett.* 125:3, 1995), and terpene synthases).

It is understood that, using the methods described herein, a multiplicity of partially double stranded complexes can be generated that comprise sequence corresponding to a specified protein domain (or part of a domain), wherein each partially double stranded complex further comprises sequences not necessarily related to the specified domain. For example, partially double stranded complex can be prepared that are comprise a kinase domain but are otherwise not necessarily related (e.g., receptor sequence, intracellular kinase, etc.).

Partially double stranded complexes and/or recipient molecules can also include nucleic acids corresponding to "linker" amino acids (generally, non-native nucleic acid sequence), which may reflect nucleic acids added during hybridization and recombining steps, as described herein.

Partially double stranded complexes and/or recipient molecules can also include nucleic acids corresponding to sequences capable of directly or indirectly regulating expression of a recombined molecule (or even of a second molecule or pathway of molecules), as further described herein. For example, partially double stranded complexes and/or recipient molecules may comprise sequences corresponding to an sequence element relating to or regulating transcription and/or expression, such as a promoter. Such elements may be known (in the sense that the sequence is known to be involved with transcription and/or expression) or may be novel. Methods for identifying novel elements (or novel arrangements of elements) are known in the art, and are briefly described below. In another example, partially double stranded complex and/or recipient molecules may comprise sequences corresponding to a small untranslated RNA, wherein such RNA, for example, is involved in regulation of gene expression.

Partially double stranded DNA comprising a 3' single stranded portion prepared according to the methods described herein can be generated from RNA copies of genomic DNA, and would thus include untranscribed sequences generally not found in mRNA, such as introns, regulatory and control elements, pseudo-genes, etc.

In some embodiments, recipient molecules (which may be single or double stranded) comprise sequence element relating to or regulating transcription and/or expression (in vivo, e.g. in a host cell, or in vitro), including at least the following: transcriptional control sequences, RNA splicing control sequences, other RNA modification control sequences, and/or translational control sequences. A wide variety of such transcription and/or translation and/or expression control sequences are well known in the art (see, for example, Sambrook et al., *Molecular Cloning: A Laboratory Manual,* 2nd ed., Cold Spring Harbor Press, Cold Spring Harbor, 1989).

Partially double stranded complex and/or recipient molecules can also include nucleic acids corresponding to untranslated RNA sequences, including tRNA, ribosomal RNA, and untranslated RNA sequences involved in, for example, disease processes and/or gene regulation as described above. Thus, partially double stranded DNA comprising a 3' single stranded portion prepared according to the methods described herein can be generated from RNA copies of genomic DNA, and would thus include untranscribed sequences generally not found in mRNA, such as introns, regulatory and control elements, pseudo-genes, etc. Partially double stranded DNA comprising a 3' single stranded portion can also be generated from exogenous elements present within a genome, such as viral sequences or any of RNA sequences which are the products of non coding sequences of either known or yet unknown functions.

Partially double stranded complexes and/or recipient molecules can also include nucleic acids corresponding to a detectable protein moiety (e.g., an enzyme moiety that catalyzes a detectable reaction such as color change or induction of fluorescence or luminescence; a moiety that interacts with a known monoclonal antibody, etc.), a moiety that allows ready purification of any polypeptide encoded by the recombined polynucleotide molecule (e.g., a tag such as GST domain, flag domain, six-cys domain, a copper chelate domain, etc.). In a preferred embodiment, the recipient molecule comprises such nucleic acids sequences.

Examples of further nucleic acid sequences that are useful in the present invention include: vector sequences (including expression vector sequences), vectors including a reporter gene or selectable marker, vectors including a "tag"; linear plasmid sequences, linker oligonucleotides, and the like. Suitable vector sequences are well known in the art. See Sambrook et al., *Molecular Cloning: A Laboratory Manual,* 2nd ed., Cold Spring Harbor Press, Cold Spring Harbor, 1989. Generally, such nucleic acids are included in recipient molecule, which is generally (but not necessarily) single stranded.

The methods of the invention further comprise hybridizing the 3' single stranded portion of a partially double stranded complex (prepared according to the methods of the invention) with a recipient nucleic acid molecule, whereby a hybrid nucleic acid is generated. (Stated alternatively, partially double-stranded complex and recipient are combined under conditions that allow hybridization.) As used herein, a hybrid nucleic acid molecule refers to hybridized partially double stranded complex and recipient molecule (which may be a second partially double stranded complex of the invention). The hybrid molecule has a nick (created adjacent hybridized 3' end of a partially double stranded complex and 5' end of the recipient molecule, or the converse) or a gap, created as when, for example, the length of hybridizable sequence is less than the length of the 3' overhang, or when the nucleotides at the 3' end of duplex and/or 5' end of recipient molecule are not hybridized. Accordingly, and as noted elsewhere, reference to hybridization of the single stranded 3' portion of the complex refers to hybridization of part of (a portion of) or the entire 3' portion.

Hybridization of 3' ends depends on a number of factors, including length of hybridizable portion and the sequence of the 3' ends. The minimum length of overlap necessary for hybridization of two 3' ends is: about 2 nucleotides, and can be at least 3, at least 4, at least 5, at least 10, or more nucleotides in length. Overlap of hybridizing portion can be at least 2, 5, 10, 20, 30, 50, 70, or 100 or more nucleotides in length. Overlap as used herein can include hybridized 3' ends comprising hybridized portions interspersed (or adjacent to) portions not capable of hybridizing.

Design considerations for the sequence of the 3' end are discussed herein, and include at least the following: use of defined or relatively defined 3' ends (e.g., corresponding to a sequence or group of related sequences); use of random portions; use of nucleotides likely or less likely to hybridize (such as increased or decreased G:C content, use of nucleotide analogs and the like). Generally, the more related (in terms of complementarity) the 3' ends are, the smaller the number of potentially hybridizable 3' ends there are. Correspondingly, the use of 3' ends comprising random portions (in partially double stranded complex and/or recipient molecule) increases the number of potentially hybridizable 3' ends is created. Other factors for increasing (or decreasing) number of potentially hybridizable 3' ends are known in the art, and discussed herein. As is well known in the art, the degree of complementarity between two sequences contributes to hybridization.

Hybridization of 3' ends includes hybridization under conditions of different "stringency". Generally, the more stringent are the hybridization conditions, the higher the sequence identity between the hybridizing 3' ends. Thus, hybridization under conditions of reduced stringency (e.g., moderate stringency, low stringency) generally results in an increase of potentially hybridizable 3' ends, and an attendant increase in the number of possible combinations between partially double stranded complex(es) and recipient molecule(s).

Hybridization is well known and understood in the art, and depends on other factors such as, for example, ionic strength and temperature. Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

Generally, the sequence of hybridizable 3' ends (of a partially double stranded complex and recipient molecule) are at least about 45%, about 50%, about 55%, about 60%, about 65%, about 70%, about 75%, about 80%, about 85%, about 95%, about 95% complementarity.

For convenience, hybridization of only one partially double stranded complex and one recipient molecule is described (and illustrated in FIGS. 3–6). It is understood that the methods of the invention are useful not only for producing hybrid molecules comprising a partially double stranded complex (according to the methods described herein) and one recipient molecule (which can be a partially double stranded complex as described herein), but also for producing hybrid molecules comprising more than partially double stranded complex and or recipient molecules. Accordingly, the invention provides for hybrid molecules comprising at least two partially double stranded complex and at least one recipient molecule, as described herein.

Recombining Hybrid Polynucleotide

In another aspect, the invention provides methods for generation of a recombined polynucleotide from hybrid polynucleotide(s) prepared according to the methods of the invention. Recombined polynucleotides are useful, for example, for screening and/or selecting for desirable properties, as further described herein. As used herein "recombined product" refers to a continuous (fully linked) polynucleotide comprising sequences corresponding to the partially double stranded complex comprising a 3' single stranded portion and the recipient molecule.

The invention provides methods for recombination of hybrid polynucleotides. Recombination can be according to the methods of the invention described herein. It is also contemplated that any method known in the art can be used. As described herein, hybrid nucleic acid molecule refers to hybridized partially double stranded complex and recipient molecule (which may be a second partially double stranded complex of the invention). The hybrid molecule has a nick (created between an adjacent hybridized 5' end of the recipient molecule (hybridized to 3' overhang of the partially double stranded complex) and a 3' end of partially double stranded complex), or a gap, created as when, for example, the length of hybridized 5' end of the recipient molecule is less than the length of the 3' overhang. Although a nick or gap is described on only one strand of a hybrid molecule, it is understood that a nick or gap may be created on both strands of a hybrid molecule (generally, when a recipient molecule is double stranded).

For convenience, the embodiments described herein generally related to a partially double stranded complex comprising a single 3' overhang hybridized to a 3' overhang of a recipient (which may be double or single stranded). Generally, in this configuration (and as illustratively diagrammed in FIGS. 3–6), the 3' overhang of recipient molecule is hybridized to the 3' single stranded portion of the partially double stranded complex, and as such, the 3' overhang of the recipient molecule can serve as a primer for primer extension. It is understood, however, that (unless specifically stated), the methods described herein apply to embodiments (e.g., partially double stranded complex with two 3' overhangs, recipient molecules comprising two 3' overhangs, and the like) in which a 3' overhang of partially double stranded complex can serve as a primer for primer extension.

In some embodiments, recombined product is generated by ligating the 3' end of the recipient molecule (which, as noted above, can also serve as a primer) with the 5' end of the non-overhanging strand of the partially double stranded complex using a DNA ligase. Suitable conditions and ligases (e.g., *E. coli* DNA ligase) are known in the art. If a 5' end ribonucleotide remains on the non-overhanging strand of the partially double stranded complex (i.e. at least one ribonucleotide of the composite primer remains following cleavage of RNA from a RNA/DNA heteroduplex), the ribonucleotide can be removed by addition of RNase H (for example, *E. coli* RNase H or T4 RNAse H), which is known to cleave the ribonucleotides added by extension of Okazaki fragments in normal lagging strand replication. See, Bhagwat M and Nossal N (2001) *J. Bio. Chem.* 276: 28516–24.

In other embodiments, recombined product is generated by (a) primer extension from hybridized 3' end of recipient molecule, whereby the gap is filled, and (b) ligation as described herein. In other embodiments, the recombined product is generated by (a) primer extension from hybridized 3' end of the complex, whereby the gap is filled, and (b) ligation as described herein. In other embodiments, recombined product is generated by (a) primer extension from hybridized 3' end of recipient molele and 3' end of the complex, whereby the gap is filled, and (b) ligation as described herein. Generally, primer extension is by a DNA polymerase lacking strand displacement activity. As further described herein, a low fidelity DNA-dependent DNA polymerase or RNA-dependent DNA polymerase (e.g., lacking proofreading capability) can be used if introduction of new mutations is desired during primer extension. Addition of new mutations results in greater diversity in the products.

In some embodiments, recombined product is generated by primer extension from hybridized 3' end of recipient molecule (and/or 3' end of hybridized complex) using a DNA polymerase comprising strand displacement activity, and displacement of the hybridized non-overlapping strand of partially double stranded complex. In some embodiments, a low fidelity polymerase comprising strand displacement activity is used, such that additional mutations are added during primer extension.

In some embodiments, recombined product is generated by nick translation (which can extend along part or all of a strand, generally a complementary strand). In some embodiments, the polymerase comprises a strand displacement activity with or without 3' and/or 5' exonuclease activity. When a polymerase with 3' exonuclease activity is used, it is desirable to add the polymerase after hybridization, to prevent degradation of the 3' single-stranded overhang.

In some embodiments, hybrid molecules are treated with agents (generally enzymes) comprising a 3' and or 5' exonuclease activity, whereby a free 3' end of recipient molecule and/or the 5' end of the non-overlapping strand of double stranded duplex are removed to varying extents, creating gaps of increased size. Exonuclease treatment of hybrid molecules, followed by gap-filling using low fidelity polymerases result in the introduction of mutations in a larger portion of the recombined product.

In another aspect of the invention, recombined molecules are generated from hybrid molecule comprising hybridized partially double stranded complex and single stranded recipient molecule (which may be immobilized, as further described herein). In some embodiments, the single stranded recipient molecule may be converted to a double stranded nucleic acid by extension with DNA polymerase (primed by hybridized 3' overhang portion of partially double stranded DNA complex). Other embodiments are described herein in the section describing immobilized recipient molecules, infra.

Figure 3:
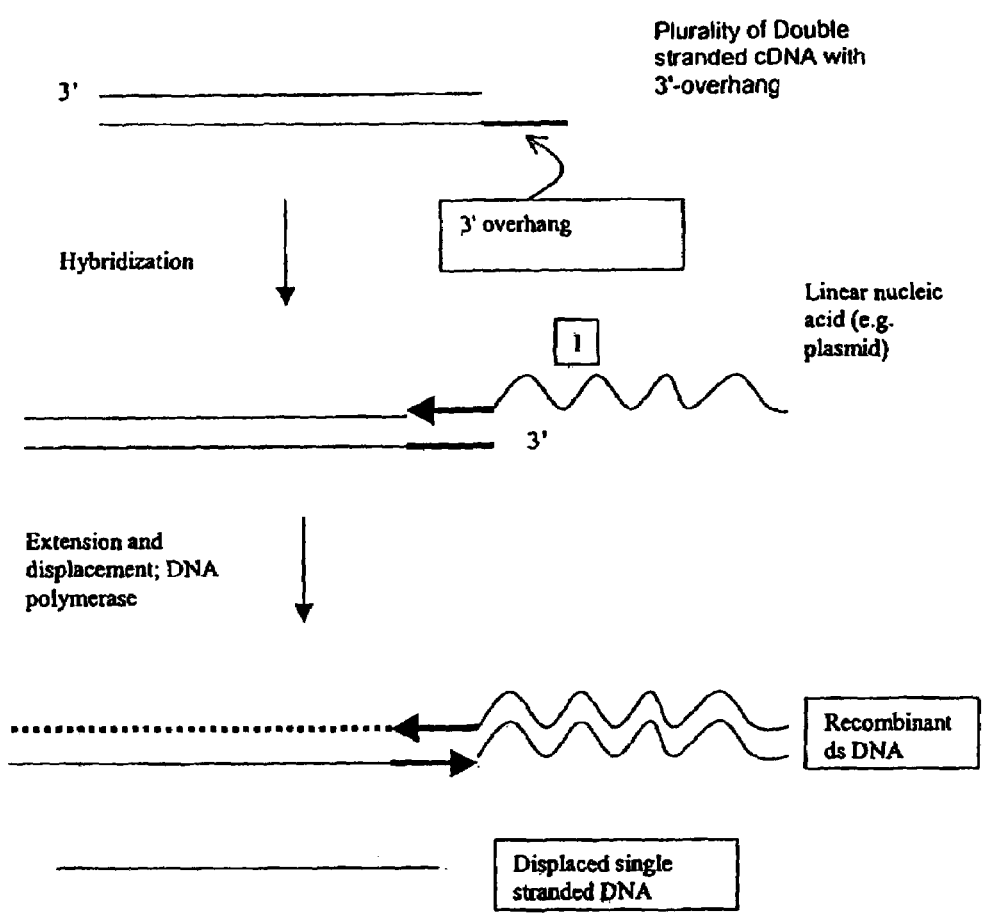
FIG. 3: shows a diagrammatic representation of a method using a complex of first and second primer extension products comprising a 3' overhang prepared according to methods of the invention.

FIG. 3 illustratively exemplifies one embodiment of the methods for generating recombined product as follows:
1. Partially double stranded complexes with 3' single-stranded overhang sequences are hybridized to a plurality of recipient molecules comprising partially double stranded DNA fragments generated by restriction digest, wherein the "sticky ends" produced from the restriction digest are capable of hybridizing with the 3' single-stranded overhang sequences of the first plurality of partially double stranded complexes;
2. Extension by DNA polymerase is used to fill gaps (if any);
3. Ligation of hybridized ends generates recombined double stranded product.

Figure 4:
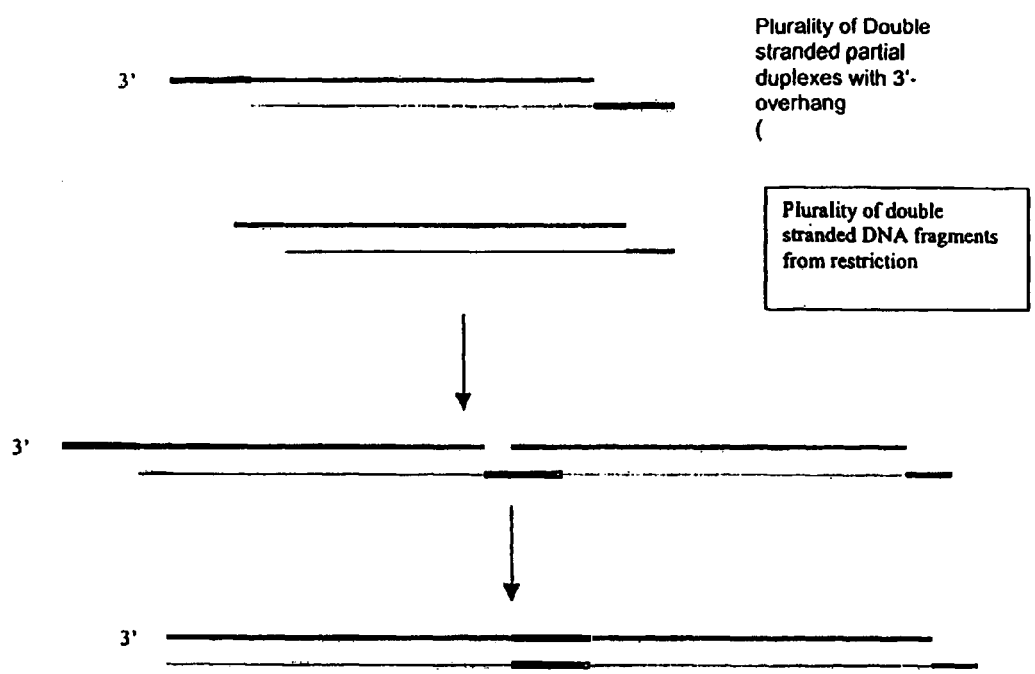
FIG. 4: shows a diagrammatic representation of a method using complex of first and second primer extension products comprising a 3' overhang prepared according to methods of invention.

FIG. 4 illustratively exemplifies one embodiment of the methods for generating recombined product as follows:
1. Partially double stranded complexes with 3' single-stranded overhang sequences are hybridized to a recipient molecules comprising single stranded nucleic acid sequences;
2. Extension by primer extension to fill gaps (if any) and ligation of hybridized ends to generate recombined single stranded product;

primer extension primed by 3' overhang of the partially double stranded complex whereby double stranded recombined product is generated.

FIG. 5 illustratively exemplifies one embodiment of the methods for generating recombined product as follows:
1. Partially double stranded complexes comprising random 3' single-stranded overhangs are hybridized to a recipient molecules comprising random 3' overhang sequences;
2. Extension by primer extension to fill gaps (if any) and ligation of hybridized ends to generate recombined single stranded product.

Uses for Recombined Products of the Invention

Recombined products are useful for screening and/or selecting products with useful properties. Methods for screening and selecting are well-known in the art. See, e.g., U.S. Pat. Nos. 5,830,721; 6,335,160; 6,344,356; 5,811,238; Zhang et al. (1997) PNAS 94:4504–4509; Gulik and Fahl (1995) PNAS 92:8140–8144; You and Arnold (1996) Protein Eng.9:77–83; Barbas (1994) PNAS 91:3809–3813; Crameria et al. (1997) Nature Biotech. 15:436–438; Heim and Tsien (1996) Curr. Biol. 6:178–182.

Generally, recombined molecules may be expressed using methods well known in the art. For example, recombined molecules can be cloned into a plasmid or expression vector, amplified by PCR, or permitted to recombine in vivo (for example, by transfection into a suitable host). Recombined molecules can be translated, followed by screening or selection (in vivo or in vitro) for desired characteristics, using procedures that are known in the art. Desirable characteristics include: enhanced and/or altered and/or hybrid enzymatic activities; enhanced or improved folding of a protein domain; ability to regulate translation and/or expression of a reporter (e.g., promoter trapping) and/or a desired phenotype and/or encoding a protein having an advantageous predetermined property. It is understood that recombined molecules can be screened or selected independent of translation of recombined sequences, as when, for example, untranslated RNA or RNA interference is assessed or other RNA molecules which are the products of non-coding sequences and function in gene expression regulation.

Generation of Recombined Nucleic Acid Attached to a Solid (or Semi-solid) Support The methods of the invention provide for generation of an immobilized recombined single or double stranded polynucleotide (such as DNA) to a support, which may be solid or semi-solid. FIG. 6 illustrates one embodiment of the invention. Hybridization of the 3' single stranded portions of the partially double stranded complex and an immobilized single stranded recipient molecule results in generation of a hybrid nucleic acid comprising a complex of the partially double stranded complex and the immobilized single stranded recipient molecule. As used herein, a "cDNA" is (i.e., encompasses) a polynucleotide. Primer extension primed by the 3' hybridized end of the single stranded recipient molecule results in displacement of the previously hybridized non-overlapping strand of partially double stranded complex (corresponding to first strand cDNA) and formation of a complex comprising (a) immobilized chimeric single stranded DNA comprising (i) the first single stranded (DNA) nucleic acid and (ii) the first strand cDNA; and (b) second primer extension product. Denaturation or degradation of the hybridized second primer extension product results in immobilized single stranded chimeric DNA.

The immobilized recipient molecule is immobilized by using methods known in the art, which include: attachment to a solid or semisolid support, e.g., paper, glass, plastic (e.g., polypropylene, nylon, polystyrene), polyacrylamide, nitrocellulose, silicon or other metals, optical fiber. A solid or semi-solid support can be configured in any means known in the art, including in a planar (e.g., glass plates, silicon chips) or three-dimensional (e.g., pins, fibers, beads, particles, microtiter wells, capillaries) configuration.

Means for attaching and/or immobilizing nucleic acids to a solid support include (i) in situ synthesis (e.g., high-density oligonucleotide arrays) using photolithographic techniques (see, Fodor et al., *Science* (1991), 251:767–773; Pease et al., *Proc. Natl. Acad. Sci. U.S.A.* (1994), 91:5022–5026; Lockhart et al., *Nature Biotechnology* (1996), 14:1675; U.S. Pat. Nos. 5,578,832; 5,556,752; and 5,510,270); (ii) spotting/printing at medium to low-density on glass, nylon or nitrocellulose (Schena et al, *Science* (1995), 270:467–470, DeRisi et al, *Nature Genetics* (1996), 14:457–460; Shalon et al., *Genome Res.* (1996), 6:639–645; and Schena et al., *Proc. Natl. Acad. Sci. U.S.A.* (1995), 93:10539–11286); (iii) by masking (Maskos and Southern, *Nuc. Acids. Res.* (1992), 20:1679–1684) and (iv) by dot-blotting on a nylon or nitrocellulose hybridization membrane (see, e.g., Sambrook et al., Eds., 1989, Molecular Cloning: A Laboratory Manual, 2nd ed., Vol. 1–3, Cold Spring Harbor Laboratory (Cold Spring Harbor, N.Y.)). Oligonucleotide primers may also be noncovalently immobilized on the support by hybridization to anchors, by means of magnetic beads, or in a fluid phase such as in microtiter wells or capillaries.

In one embodiment of the method, recipient nucleic acids are immobilized as a microarray.

Optionally, labels may be attached to one or both strands of the partially double stranded complex, or to the immobilized recipient molecule, or to the solid support to which the recipient molecule is attached (e.g., beads with attached dye molecules), or any combination or permutation thereof. Labeling allows the identification and/or quantification of the immobilized recipient molecule which bind partially double stranded complex and/or which form further products. Labels include fluorochromes or radioisotopes. The label may also be a small molecule which is a member of a specific binding pair, and can be detected following binding of the other member of the specific binding pair, such as biotin and streptavidin, respectively, with the last member of the binding pair conjugated to an enzyme that catalyzes the generation of a detectable signal that could be detected by methods such as colorimetry, fluorometry or chemiluminescence. All of the above examples are well known in the art.

Generation of a hybrid molecule comprising immobilized double or single stranded recipient molecules is by any method described herein.

Generally, production of a recombined immobilized polynucleotide (which can be double or single stranded) is accomplished by any method described herein.

In other embodiments, immobilized recombined product is rendered double stranded by primer extension primed by the hybridized 3' overhang of partially double stranded complex.

In other embodiments, immobilized partially double stranded recombined product is generated by primer extension primed by the hybridized 3' overhand of partially double stranded complex which is halted before the end of the 3' overhang strand is reached, in which case immobilized double stranded DNA with a 5' overhang is produced.

In other embodiments, 5' and/or 3' exonucleases can be used to remove part or all of the non-overlapping strand of double stranded heteroduplex (after, for example, primer extension and/or ligation. Such manipulations can result in production of single stranded recombined product that is shorter than the length of a combined partially double stranded complex and recipient molecule.

In other embodiments, following generation of a recombined strand that is immobilized (generally present in a complex comprising the 3' overhang strand of the partially double stranded complex), the 3' overhang strand of the original partially double stranded complex is removed to produce immobilized recombined product. Removal of the 3' overhang strand of partially double stranded complex may be achieved by denaturing the two strands through thermal denaturation or any other method known in the art, such as alkali treatment.

In other embodiment, the 3' overhang strand of the original partially double stranded complex can be partially or completely removed by degrading the 3' overhang strand using exonuclease; such as 5' exonuclease. Such 5' exonucleases and conditions for their use are known in the art. This procedure, if carried out from the 5' end of the 3' overhang strand and not allowed to go to completion, results in formation of an immobilized partially double stranded complex with a free 3' overhang.

Uses of Immobilized Recombined Product

Uses of such immobilized polynucleotides (which can be double stranded or single stranded) will be readily apparent to those of skill in the art. In some embodiments, the methods of the invention may be used to provide an array containing a large number of different polynucleotide probes where the sequence and location of each probe is known. Such arrays are useful, for example, in expression analysis, either of a single sample or of multiple samples which may be compared. See e.g., U.S. Pat. Nos. 6,344,316 and 6,303,301. In other embodiments, the solid support may be a bead that may be further dyed as a reporter group, offering means for identifying and/or quantifying levels of, e.g., mRNA. In yet other embodiments, single stranded DNA attached to the solid support may be used to sequence the single stranded DNA, by sequencing by synthesis (e.g. pyrosequencing). It is also possible to use the attached single stranded composition for selection of desired sequences from a mixture of sequences, by hybridization to the desired sequences, for example, if the attached single stranded sequences comprise sequences of expressed genes of one sample, it is possible to use the solid support with the attached single strand for selection of similar sequences from mRNA or cDNAs derived from another sequence. The attached single stranded polynucleotides may be one sequence or a plurality of sequences.

Kits

The invention also includes kits that are useful in methods of recombination of nucleic acids or directed evolution. Reagents that are useful for the practice of the present invention may desirably be provided together and assembled into a kit. Kits of the invention include partially double stranded complexes with 3' overhang sequences made by the method(s) described herein) and instructions for use in any of the methods described herein (and may further include components, such as appropriate enzyme(s), for achieving recombination). In some embodiments, the partially double stranded complexes comprise a cDNA library, full-length or partial domains for exon shuffling, or fragments of a coding sequence, for DNA shuffling. In some embodiments, the kits also comprise DNA polymerase. In some embodiments, the kits contain instructions for recombining the nucleic acids as described herein. In some embodiments, the kits comprise a solid support.

Components and Reaction Conditions Used in the Methods of the Invention

Template Nucleic Acid

The RNA target includes RNAs from any source in purified or unpurified form, which can be RNA such as total RNA, tRNA, mRNA, rRNA, mitochondrial RNA, chloroplast RNA, DNA-RNA hybrids, or mixtures thereof, from any source and/or species, including human, animals, plants, and microorganisms such as bacteria, yeasts, viruses, viroids, molds, fungi, plants, and fragments thereof. It is understood that the RNA can be coding or noncoding RNA (such as untranslated small RNAs). RNAs can be obtained and purified using standard techniques in the art. Use of a DNA target (including genomic DNA target) would require initial transcription of the DNA target into RNA form, which can be achieved using methods disclosed in Kurn, U.S. Pat. No. 6,251,639 B1, and by other techniques (such as expression systems) known in the art. Thus, partially double stranded complex can be generated from RNA target that is itself generated from a DNA source (such as genomic DNA), using methods known in the art, including Kurn, U.S. Pat. No. 6,251,639. RNA copies of genomic DNA would generally include untranscribed sequences generally not found in mRNA, such as introns, regulatory and control elements, etc. RNA targets may also be generated from cloned genomic DNA sequences that can be subjected to in vitro transcription. Use of a DNA-RNA hybrid would require denaturation of the hybrid to obtain a single stranded RNA, denaturation followed by transcription of the DNA strand to obtain an RNA, or other methods known in the art such as digestion with an RNAse H to generate single stranded DNA. The target RNA can be only a minor fraction of a complex mixture such as a biological sample and can be obtained from various biological materials by procedures well known in the art. The target RNA can be known or unknown and may contain more than one desired specific nucleic acid sequence of interest, each of which may be the same or different from each other. Denaturation may also be carried out to remove secondary structure present in a RNA target molecule. If the target nucleic acid is double stranded (e.g., RNA/DNA hybrid) the initial step could be target denaturation. The denaturation step may be thermal denaturation or any other method known in the art. The removal of DNA strands from a complex material may be also achieved by treatment with DNase.

Composite Primer

The methods of the invention employ a composite primer that is composed of RNA and DNA portions. The composite primer can be designed such that subsequent displacement of the primer extension product by binding of a new nucleic acid capable of priming primer extension.

Composite primers for use in the methods and compositions of the invention comprise a sequence capable of hybridizing to a target RNA. The sequence that is capable of hybridizing to the target RNA can be based on the particular sequence of a specific target RNA (for e.g., the mRNA of a particular gene), or be based on a more general sequence type known to be present in a plurality of RNA species, such as the poly-A tail sequence generally believed in the art to be present in all eukaryotic mRNA. In addition, the sequence that is capable of hybridizing to the target RNA may comprise a sequence complementary to the poly-A tail of mRNA, and may further comprise additional random sequences (generally not complementary to a poly-A sequence) at the 3' end of the 3' portion.

The sequence that is capable of hybridizing to the target RNA may also comprise a random sequence. Random primers are well known in the art, and include at least the following: primers hybridizable to two or more sequences in a sample; and primers comprising poly-dT sequences that are hybridizable to a multiplicity of RNAs in a sample (such as all mRNA). For convenience, a single random composite primer is discussed above. However, it is understood that the term "random primer" can refer to a primer that is a member of a population of primers which are collectively designed to a desired and/or significant population of target sequences.

It is also understood that generation of partially double stranded complexes from a plurality of mRNA species in a single reaction mixture may, but not necessarily, employ a multiplicity, or a large multiplicity, of primers. Thus, the invention contemplates the use of a multiplicity of different composite primers (random or non-random) when partially double stranded complexes of the invention are generated from a plurality of mRNA species in a single reaction mixture.

In some embodiments, a first composite primer is used in the methods of the invention. In other embodiments, a multiplicity of different first composite primers are used in the methods of the invention. In other embodiments, a first and second composite primer are used in the methods of the invention. The second composite primer (used to primer second strand synthesis) may comprise some or all of the sequence of the first composite primer, and the first composite primer may comprise some or all of the sequence of the second composite primer. In some embodiments, the second composite primer comprises a different sequence than the first composite primer. In other embodiments, a multiplicity of different second composite primers are used in the methods of the invention.

The composite primer may comprise a sequence, preferably at the 5' end, that is not hybridizable (under a given set of conditions) to the target (for example, a non-hybridized 5' portion that would constitute a tail when the primer is bound to the target). Individual DNA and RNA portions of the composite primer may be completely or partially hybridizable to the target RNA.

Generation of primers suitable for extension by polymerization is well known in the art, such as described in PCT Pub. No. WO99/42618 (and references cited therein). The composite primer comprises a combination of RNA and DNA (see definition above), with the 3'-end nucleotide being a nucleotide suitable for nucleic acid extension. The 3'-end nucleotide can be any nucleotide or analog that when present in a primer, is extendable by a DNA polymerase. Generally, the 3'-end nucleotide has a 3'-OH. Suitable primers include those that comprise at least one portion of RNA and at least one portion of DNA. For example, composite primers can comprise a 5'-RNA portion and a 3'-DNA portion (in which the RNA portion is adjacent to the 3'-DNA portion); or 5'- and 3'-DNA portions with an intervening RNA portion. Accordingly, in one embodiment, the composite primer comprises a 5' RNA portion and a 3'-DNA portion, preferably wherein the RNA portion is adjacent to the 3'-DNA portion. In another embodiment, the composite primer comprises 5'- and 3'-DNA portions with at least one intervening RNA portion (i.e., an RNA portion between the two DNA portions). In yet another embodiment, the composite primer of the invention comprises a 3'-DNA portion and at least one intervening RNA portion (i.e., an RNA portion between DNA portions).

The length of an RNA portion in a composite primer comprising a 3'-DNA portion and an RNA portion can be from about 1 to about 50 or more nucleotides, from about 3 to about 20, from about 4 to about 15, and about 5 to about 10 nucleotides. In some embodiments of a composite primer comprising a 3'-DNA portion and an RNA portion, an RNA portion can be at least about any of 1, 3, 4, 5 nucleotides, with an upper limit of about any of 10, 15, 20, 25, 30, 50, 75, 100, 125, 150, or more nucleotides. In some embodiments, the RNA portion of the composite primer consists of about 10 to about 20 nucleotides. In some embodiments, the RNA portion of the composite primer consists of about 10 to about 20 nucleotides and the DNA portion of the composite primer consists of about 5 to about 20 nucleotides.

The length of the 5'-RNA portion in a composite primer comprising a 5'-RNA portion and a 3'-DNA portion can be from about 2 to about 50 or more nucleotides, from about 5 to about 20 nucleotides, from about 7 to about 18 nucleotides, preferably from about 8 to about 17 nucleotides, and from about 10 to about 15 nucleotides. In other embodiments of a composite primer comprising a 5'-RNA portion and a 3'-DNA portion, the 5'-RNA portion can be at least about any of 3, 5, 7, 8, 10 nucleotides, with an upper limit of about any of 15, 17, 18, 20, 50, 75, 100, 125, 150, or more nucleotides.

In embodiments of a composite primer comprising a 5'-RNA portion and a 3'-DNA portion further comprising non-5'-RNA portion(s), a non-5'-RNA portion can be from about 1 to about 7 nucleotides, from about 2 to about 6 nucleotides, and from about 3 to about 5 nucleotides. In certain embodiments of a composite primer comprising a 5'-RNA portion and a 3'-DNA portion further comprising non-5'-RNA portion(s), a non-5'-RNA portion can be at least about any of 1, 2, 3, 5, with an upper limit of about any of 5, 6, 7, 10, 15, 20, 25, 30, or more nucleotides.

In embodiments of a composite primer comprising a 5'-RNA portion and a 3'-DNA portion, in which the 5'-RNA portion is adjacent to the 3'-DNA portion, the length of the 5'-RNA portion can be from about 3 to about 50 or more nucleotides, from about 5 to about 20 nucleotides, from about 7 to about 18 nucleotides, from about 8 to about 17 nucleotides, and from about 10 to about 15 nucleotides. In certain embodiments of a composite primer comprising a 5'-RNA portion and a 3'-DNA portion, in which the 5'-RNA portion is adjacent to the 3'-DNA portion, the 5'-RNA portion can be at least about any of 3, 5, 7, 8, 10 nucleotides, with an upper limit of about any of 15, 17, 18, 20, 50, 75, 100, 125, 150, or more nucleotides.

The length of an intervening RNA portion in a composite primer comprising 5'- and 3'-DNA portions with at least one intervening RNA portion can be from about 1 to about 7 nucleotides, from about 2 to about 6 nucleotides, and from about 3 to about 5 nucleotides. In some embodiments of a composite primer comprising 5'- and 3'-DNA portions with at least one intervening RNA portion, an intervening RNA portion can be at least about any of 1, 2, 3, 5 nucleotides, with an upper limit of about any of 5, 6, 7, 10, 15, 20, 25, 30, or more nucleotides. The length of an intervening RNA portion in a composite primer comprising a 3'-DNA portion and at least one intervening RNA portion can be from about 1 to about 7 nucleotides, from about 2 to about 6 nucleotides, and from about 3 to about 5 nucleotides. In some embodiments of a composite primer comprising a 3'-DNA portion and at least one intervening RNA portion, an intervening RNA portion can be at least about any of 1, 2, 3, 5 nucleotides, with an upper limit of about any of 5, 6, 7, 10, 15, 20, 25, 30 or more nucleotides. In a composite primer comprising a 3'-DNA portion and at least one intervening RNA portion, further comprising a 5'-RNA portion, the 5'-RNA portion can be from about 3 to about 25 nucleotides, from about 5 to about 20 nucleotides, from about 7 to about 18 nucleotides, about 8 to about 17 nucleotides, and from about 10 to about 15 nucleotides. In some embodiments of a composite primer comprising a 3'-DNA portion and at least one intervening RNA portion, further comprising a 5'-RNA portion, the 5'-RNA portion can be at least about any of 3, 5, 7, 8, 10 nucleotides, with an upper limit of about any of 15, 17, 18, 20, 25, 30, or more nucleotides.

The length of the 3'-DNA portion in a composite primer comprising a 3'-DNA portion and an RNA portion can be from about 1 to about 20, from about 3 to about 18, from about 5 to about 15, and from about 7 to about 12 nucleotides. In some embodiments of a composite primer comprising a 3'-DNA portion and an RNA portion, the 3'-DNA portion can be at least about any of 1, 3, 5, 7, 10 nucleotides, with an upper limit of about any of 10, 12, 15, 18, 20, 22, 25, 30, 35, or more nucleotides.

The length of the 3'-DNA portion in a composite primer comprising a 5'-RNA portion and a 3'-DNA portion can be from about 1 to about 20 nucleotides, from about 3 to about 18 nucleotides, from about 5 to about 15 nucleotides, and from about 7 to about 12 nucleotides. In some embodiments of a composite primer comprising a 5'-RNA portion and a 3'-DNA portion, the 3' DNA portion can be at least about any of 1, 3, 5, 7, 10 nucleotides, with an upper limit of about any of 10, 12, 15, 18, 20, 22, 25, 30, 35, or more nucleotides.

In embodiments of a composite primer comprising a 5'-RNA portion and a 3'-DNA portion, further comprising non-3'-DNA portion(s), a non-3'-DNA portion can be from about 1 to about 10 nucleotides, from about 2 to about 8 nucleotides, and from about 3 to about 6 nucleotides. In some embodiments of a composite primer comprising a 5'-RNA portion and a 3'-DNA portion, further comprising non-3'-DNA portion(s), a non-3'-DNA portion can be at least about any of 1, 2, 3, 5 nucleotides, with an upper limit of about any of 6, 8, 10, 12, 15, 25, 30, 35 or more nucleotides.

In embodiments of a composite primer comprising a 5'-RNA portion and a 3'-DNA portion in which the 5'-RNA portion is adjacent to the 3'-DNA portion, the length of the 3'-DNA portion can be from about 1 to about 20 nucleotides, from about 3 to about 18 nucleotides, from about 5 to about 15 nucleotides, and from about 7 to about 12 nucleotides. In certain embodiments of the primer comprising a 5'-RNA portion and a 3'-DNA portion in which the 5'-RNA portion is adjacent to the 3'-DNA portion, the 3'-DNA portion can be at least about any of 1, 3, 5, 7, 10 nucleotides, with an upper limit of about any of 10, 12, 15, 18, 20, 22, 25, 30, 35, or more nucleotides.

The length of a non-3'-DNA portion in a composite primer comprising 5'- and 3'-DNA portions with at least one intervening RNA portion can be from about 1 to about 10 nucleotides, from about 2 to about 8 nucleotides, and from about 3 to about 6 nucleotides. In some embodiments of a primer comprising 5'- and 3'-DNA portions with at least one intervening RNA portion, a non-3'-DNA portion can be at least about any of 1, 2, 3, 5 nucleotides, with an upper limit of about any of 6, 8, 10, 12, 15, 20, 25, 30, or more nucleotides.

The length of the 3'-DNA portion in a composite primer comprising 5'- and 3'-DNA portions with at least one intervening RNA portion can be from about 1 to about 20 nucleotides, from about 3 to about 18 nucleotides, from about 5 to about 15 nucleotides, and from about 7 to about 12 nucleotides. In some embodiments of a composite primer comprising 5'- and 3'-DNA portions with at least one intervening RNA portion, the 3'-DNA portion can be at least about any of 1, 3, 5, 7, 10 nucleotides, with an upper limit of about any of 10, 12, 15, 18, 20, 22, 25, 30 or more nucleotides.

The length of a non-3'-DNA portion (i.e., any DNA portion other than the 3'-DNA portion) in a composite primer comprising a 3'-DNA portion and at least one intervening RNA portion can be from about 1 to about 10 nucleotides, from about 2 to about 8 nucleotides, and from about 3 to about 6 nucleotides. In some embodiments of a composite primer comprising a 3'-DNA portion and at least one intervening RNA portion, a non-3'-DNA portion can be at least about any of 1, 3, 5, 7, 10 nucleotides, with an upper limit of about any of 6, 8, 10, 12, 15, 20, 25, 30 or more nucleotides. The length of the 3'-DNA portion in a composite primer comprising a 3'-DNA portion and at least one intervening RNA portion can be from about 1 to about 20 nucleotides, from about 3 to about 18 nucleotides, from about 5 to about 15 nucleotides, and from about 7 to about 12 nucleotides. In some embodiments of a composite primer comprising a 3'-DNA portion and at least one intervening RNA portion, the 3'-DNA portion can be at least about any of 1, 3, 5, 7, 10 nucleotides, with an upper limit of about any of 10, 12, 15, 18, 20, 22, 25, 30, or more nucleotides. It is understood that the lengths for the various portions can be greater or less, as appropriate under the reaction conditions of the methods of this invention.

In some embodiments, the 5'-DNA portion of a composite primer includes the 5'-most nucleotide of the primer. In some embodiments, the 5'-RNA portion of a composite primer includes the 5' most nucleotide of the primer. In other embodiments, the 3'-DNA portion of a composite primer includes the 3' most nucleotide of the primer. In other embodiments, the 3'-DNA portion is adjacent to the 5'-RNA portion and includes the 3' most nucleotide of the primer (and the 5'-RNA portion includes the 5' most nucleotide of the primer).

The total length of the composite primer can be from about 10 to about 50 nucleotides, from about 15 to about 30 nucleotides, and from about 20 to about 25 nucleotides. In some embodiments, the length can be at least about any of 10, 15, 20, 25, 30 nucleotides, with an upper limit of about any of 25, 30, 50, 60, 70, 75, 85, 100 or more nucleotides. It is understood that the length can be greater or less, as appropriate under the reaction conditions of the methods of this invention.

To achieve hybridization to a target nucleic acid (which, as is well known and understood in the art, depends on other factors such as, for example, ionic strength and temperature), the portion of the primer that is hybridizable to the target RNA is preferably of at least about 60%, more preferably at least about 75%, even more preferably at least about 90%, and most preferably at least about 95% complementarity to the target nucleic acid.

In some embodiments, the RNA portion of the composite primer that hybridizes to target RNA is 5' with respect to the 3' DNA portion. In some embodiments, the 5' RNA portion is adjacent to the 3' DNA portion. In some embodiments, the target RNA is mRNA, and the composite primer that hybridizes to target RNA comprises a poly-dT sequence, and further comprises a 5' portion that does not hybridize to the target mRNA under conditions which the composite primer hybridizes to the target mRNA. In some embodiments, the composite primer that hybridizes to target RNA comprises a random sequence. In some embodiments, a plurality of different composite primers are used for hybridizing to the target RNA.

Second Primer

The second primer in the methods of the invention (which primes generation of the second strand cDNA) comprises a sequence (which may or may not be the whole of the primer) that is hybridizable (under a given set of conditions) to a first strand cDNA (interchangeably called first primer extension product) at a site on the first strand cDNA such that the second strand cDNA would include the RNA sequence of interest. In some embodiments, the hybridizable sequence of the second primer is designed based on a known sequence of the desired binding site on a first strand cDNA. In other embodiments, the hybridizable sequence is based on random sequences, for example, known in the art to be suitable for random priming of first strand cDNAs generated from a plurality of RNA species. In other embodiments, the second primer comprises a strand switch oligonucleotide, described in U.S. Pat. Nos. 5,962,271 and 5,962,272, which is hybridizable to the Cap sequences present on mRNA and causes the reverse transcriptase to switch from the mRNA template to the switch oligonucleotide, permitting generation of a second strand cDNA primed by the "switch oligonucleotide". Alternatively, a homopolymeric tail is added to the 3' terminus of the first primer extension product, and the second primer comprises the complement of the homopolymeric tail.

In some embodiments, the second primer (which primes generation of the second strand cDNA) is a composite primer (as described above). In these embodiments, the method involves generation of a double stranded cDNA comprising two 3' single stranded DNA portions.

To achieve hybridization to a first strand cDNA (which, as is well known and understood in the art, depends on other factors such as, for example, ionic strength and temperature), the sequence of the second primer that is hybridizable to the first strand cDNA is preferably of at least about 60%, more preferably at least about 75%, even more preferably at least about 90%, and most preferably at least about 95% complementarity to the first strand cDNA.

In some embodiments, the second primer comprises DNA. In another embodiment, the second primer comprises RNA. In yet another embodiment, the second primer comprises DNA and RNA.

In some embodiments, the second primer is provided by self priming (for example, by a hairpin loop) at the 3' end of the composite primer extension product. In these embodiments, a sequence at the 3' end of the composite primer extension product hybridizes to another sequence in the composite primer extension product itself, for example as described in U.S. Pat. No. 6,132,997. In these embodiments, said sequence at the 3' of the composite primer extension product is generally cleaved (for example, with S1 nuclease) following its hybridization to the composite primer extension product and/or its extension along the composite primer extension product. U.S. Pat. No. 6,132,997.

In some embodiments, the second primer is provided by one or more target RNA fragment(s), and as such is not an exogenously added primer. Such a target RNA fragment can be generated using methods well known in the art, including incomplete degradation (fragmentation or cleavage) of a target RNA in a complex of target RNA and first primer extension product by an agent (such as an enzyme) that cleaves RNA in an RNA/DNA hybrid, such that one or more RNA fragments remain bound to the first primer extension product. As noted above in an earlier section, cleavage/fragmentation can also be effected by heat treatment (which is not sufficient to denature or separate template RNA from first primer extension product), or chemical treatment (such as treatment under alkaline conditions). In some embodiments, cleavage giving rise to target RNA fragment(s) which serve as primer(s) is effected by RNaseH.

DNA Polymerase, an Agent Capable of Cleaving an RNA-DNA Hybrid, and RNA Polymerase DNA Polymerase, an Agent Capable of Cleaving an RNA-DNA Hybrid, and RNA Polymerase The methods of the invention employ the following enzymes: an enzyme comprising RNA-dependent DNA polymerase activity, an enzyme comprising DNA-dependent DNA polymerase activity, an agent capable of cleaving an RNA strand of an RNA-DNA hybrid (for example, a ribonuclease such as RNase H), and, in some aspects a DNA-dependent RNA polymerase. One or more of these activities may be found and used in a single enzyme. For example, RNase H activity may be supplied by an RNA-dependent DNA polymerase (such as reverse transcriptase) or may be provided in a separate enzyme. Reverse transcriptases useful for this method may or may not have RNase H activity. DNA-dependent polymerase and RNA-dependent polymerase may be provided in a single enzyme, or in two separate enzymes.

One aspect of the invention is the formation of double stranded cDNA from a primer-RNA complex. This process generally utilizes the enzymatic activities of an RNA-dependent DNA polymerase, a DNA-dependent DNA polymerase and a ribonuclease activity.

RNA-dependent DNA polymerases for use in the methods and compositions of the invention are capable of effecting extension of a primer according to the methods of the invention. Accordingly, a preferred RNA-dependent DNA polymerase is one that is capable of extending a nucleic acid primer along a nucleic acid template that is comprised at least predominantly of ribonucleotides. Suitable RNA-dependent DNA polymerases for use in the methods and compositions of the invention include reverse transcriptase. Many reverse transcriptases, such as those from avian myeoloblastosis virus (AMV-RT), and Moloney murine leukemia virus (MMLV-RT) comprise more than one activity (for example, polymerase activity and ribonuclease activity) and can function in the formation of the double stranded cDNA molecules. However, in some instances, it is preferable to employ a reverse transcriptase which lacks the RNase H activity. Reverse transcriptase devoid of RNase H activity are known in the art, including those comprising a mutation of the wild type reverse transcriptase where the mutation eliminates the RNase H activity. The addition of an RNase H from other sources, such as that isolated from $E.\ coli$, can be employed for the formation of the double stranded cDNA.

DNA-dependent DNA polymerases for use in the methods and compositions of the invention are capable of effecting extension of the composite primer according to the methods of the invention. Accordingly, a preferred polymerase is one that is capable of extending a nucleic acid primer along a nucleic acid template that is comprised at least predominantly of deoxynucleotides. The formation of the double stranded cDNA can be carried out by reverse transcriptase which comprises both RNA-dependent DNA polymerase and DNA-dependent DNA polymerase activities. DNA polymerase may or may not possess strand displacement activity. Preferably, the DNA polymerase has high affinity for binding at the 3'-end of an oligonucleotide hybridized to a nucleic acid strand. DNA polymerase may or may not possess substantial nicking activity. DNA polymerase may or may not possess 5'→3' and/or 3'→5' exonuclease activity. Generally, this exonuclease activity is dependent on factors such as pH, salt concentration, whether the template is double stranded or single stranded, and so forth, all of which are familiar to one skilled in the art. Mutant DNA polymerases in which the 5'→3' exonuclease activity has been deleted. Mutant DNA polymerases which lack both 5' to 3' nuclease and 3' to 5' nuclease activities have also been described, for example, exo$^{-/-}$Klenow DNA polymerase. In some embodiments, the use of thermostable DNA polymerases with strand displacement activity is preferred. Such polymerases are known in the art, such as described in U.S. Pat. No. 5,744,312 (and references cited therein). The polymerases can further have proofreading activity or have little or no proofreading ability Suitable DNA polymerases for use in the methods and compositions of the invention include those disclosed in U.S. Pat. Nos. 5,648,211 and 5,744,312, which include exo⁻ Vent (New England Biolabs), exo⁻ Deep Vent (New England Biolabs), Bst (BioRad), exo⁻ Pfu (Stratagene), Bca (Panvera), sequencing grade Taq (Promega), exo⁻/⁻Klenow DNA polymerase, and thermostable DNA polymerases from thermoanaerobacter thermohydrosulfuricus.

The agent (such as a ribonuclease) for use in the methods and compositions of the invention is capable of cleaving ribonucleotides in an RNA/DNA hybrid. Preferably, the ribonuclease cleaves ribonucleotides in an RNA/DNA hybrid regardless of the identity and type of nucleotides adjacent to the ribonucleotide to be cleaved. It is preferred that the ribonuclease cleaves independent of sequence identity. Examples of suitable ribonucleases for the methods and compositions of the invention are well known in the art, including ribonuclease H (RNase H), including Hybridase.

In general, the enzymes used in the methods and compositions of the invention should not produce substantial degradation of the nucleic acid components of said methods and compositions.

In some embodiments, the same enzyme comprises RNA-dependent DNA polymerase activity and cleaves RNA from an RNA/DNA hybrid. In some embodiments, the same enzyme comprises DNA-dependent DNA polymerase activity and cleaves RNA from an RNA/DNA hybrid. In some embodiments, the same enzyme comprises DNA-dependent DNA polymerase activity, RNA-dependent DNA polymerase activity and cleaves RNA from an RNA/DNA hybrid. In some embodiments, different enzymes comprise RNA-dependent DNA polymerase activity and DNA-dependent DNA polymerase activity. In some embodiments, different enzymes comprise RNA-dependent DNA polymerase activity and cleave RNA from an RNA/DNA hybrid. In some embodiments, different enzymes comprise DNA-dependent DNA polymerase activity and cleave RNA from an RNA/DNA hybrid.

Reaction Conditions and Detection

Appropriate reaction media and conditions for carrying out the methods of the invention are those that permit primer extension by polymerases, hybridization, and recombination according to the methods of the invention. Such media and conditions are known to persons of skill in the art, and are described in various publications, such as U.S. Pat. Nos. 5,554,516; 5,716,785; 5,130,238; 5,194,370; 6,090,591; 5,409,818; 5,554,517; 5,169,766; 5,480,784; 5,399,491; 5,679,512; and PCT Pub. No. WO99/42618. For example, a buffer may be Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction medium can also include bivalent metal ions such as $Mg^{2+}$ or $Mn^{2+}$, at a final concentration of free ions that is within the range of from about 0.01 to about 15 mM, and most preferably from about 1 to 10 mM. The reaction medium can also include other salts, such as KCl or NaCl, that contribute to the total ionic strength of the medium. For example, the range of a salt such as KCl is preferably from about 0 to about 125 mM, more preferably from about 0 to about 100 mM, and most preferably from about 0 to about 75 mM. The reaction medium can further include additives that could affect performance of the reactions, but that are not integral to the activity of the enzyme components of the methods. Such additives include proteins such as BSA, single strand binding proteins (for e.g., T4 gene 32 protein), and non-ionic detergents such as NP40 or Triton. Reagents, such as DTT, that are capable of maintaining enzyme activities can also be included. Such reagents are known in the art. Where appropriate, an RNase inhibitor (such as Rnasin) that does not inhibit the activity of the RNase employed in the method can also be included. Any aspect of the methods of the invention can occur at the same or varying temperatures. Preferably, the reactions generating DNA double stranded complex (particularly, primer extension other than the first and second strand cDNA synthesis steps, and strand displacement) are performed isothermally, which avoids the cumbersome thermocycling process. The reactions are carried out at a temperature that permit primer extension, hybridization, and recombination as described herein, and that does not substantially inhibit the activity of the enzymes employed. The temperature can be in the range of any of about 15° C. to about 85° C., about 25° C. to about 85° C., about 30° C. to about 80° C., and about 37° C. to about 75° C. In some embodiments that include RNA transcription (for example, when RNA target is produced from DNA), the temperature for the transcription step is lower than the temperature(s) for the following steps (such as denaturation of the RNA target). In these embodiments, the temperature of the transcription steps can be in the range of about 25° C. to about 85° C., about 30° C. to about 75° C., and about 37° C. to about 70° C. If cleavage of RNA is to be effected by heat, incubation occurs at a temperature sufficient to effect the desired cleavage without denaturation the first primer extension product (before cleavage), which can be about 65° C. to about 80° C. or about 70° C. to about 75° C. Extension is performed at a temperature suitable to preserve sufficient enzyme activity.

Nucleotide and/or nucleotide analogs, such as deoxyribonucleoside triphosphates, that can be employed for synthesis of the primer extension products in the methods of the invention are provided in the amount of from preferably about 50 to about 2500 μM, more preferably about 100 to about 2000 μM, even more preferably about 200 to about 1700 μM, and most preferably about 250 to about 1500 μM. In some embodiments, a nucleotide or nucleotide analog whose presence in the primer extension strand enhances displacement of the strand (for example, by causing base pairing that is weaker than conventional AT, CG base pairing) is included. Such nucleotide or nucleotide analogs include deoxyinosine and other modified bases, all of which are known in the art. Nucleotides and/or analogs, such as ribonucleoside triphosphates, that can be employed for synthesis of the RNA transcripts in the methods of the invention are provided in the amount of from preferably about 0.25 to about 6 mM, more preferably about 0.5 to about 5 mM, even more preferably about 0.75 to about 4 mM, and most preferably about 1 to about 3 mM.

The oligonucleotide components of the reactions of the invention are generally in excess of the number of target nucleic acid sequence. They can be provided at about or at least about any of the following: 10, $10^2$, $10^4$, $10^6$, $10^8$, $10^{10}$, $10^{12}$ times the amount of target nucleic acid. Composite primers can each be provided at about or at least about any of the following concentrations: 50 nM, 100 nM, 500 mM, 1000 nM, 2500 nM, 5000 nM.

In one embodiment, the foregoing components are added simultaneously at the initiation of the methods for generating recombined products. In another embodiment, components are added in any order prior to or after appropriate timepoints during the process, as required and/or permitted by the reaction. Such timepoints, some of which are noted below, can be readily identified by a person of skill in the art. The enzymes used for primer extension, and recombination according to the methods of the invention can be added to the reaction mixture either prior to the target nucleic acid denaturation step (denaturation in this context generally refers to subjecting target RNA to conditions which open sequence(s) to make them accessible), following the denaturation step, or following hybridization of the primer to the target RNA, following generation of double stranded complex comprising a 3' overhang, or following hybridization of double stranded complex comprising a 3' overhang to recipient molecule, as determined by their thermal stability and/or other considerations known to the person of skill in the art. The first strand cDNA (composite primer extension product) and the second strand cDNA (second primer extension product) synthesis reactions can be performed consecutively, followed by the hybridization and recombination steps. In these embodiments, the reaction conditions and components may be varied between the different reactions.

The recombination process (including generation of double stranded complex comprising a single stranded 3' overhang) can be stopped at various timepoints, and resumed at a later time. Said timepoints can be readily identified by a person of skill in the art. One timepoint is at the end of first strand cDNA synthesis. Another timepoint is at the end of second strand cDNA synthesis. Another timepoint is after generation of partially double stranded complex comprising a 3' single stranded overhang. Another timepoint is after hybridization of partially double stranded complex with recipient nucleic acids. Methods for stopping the reactions are known in the art, including, for example, cooling the reaction mixture to a temperature that inhibits enzyme activity or heating the reaction mixture to a temperature that destroys an enzyme. Methods for resuming the reactions are also known in the art, including, for example, raising the temperature of the reaction mixture to a temperature that permits enzyme activity or replenishing a destroyed (depleted) enzyme. In some embodiments, one or more of the components of the reactions is replenished prior to, at, or following the resumption of the reactions. Alternatively, the reaction can be allowed to proceed (i.e., from start to finish) without interruption.

The reaction can be allowed to proceed without purification of intermediate complexes, for example, to remove primer. Products can be purified at various timepoints, which can be readily identified by a person of skill in the art. One timepoint is at the end of first strand cDNA synthesis. Another timepoint is at the end of second strand cDNA synthesis. Another timepoint is after generation of partially double stranded complex comprising a 3' single stranded overhang. Another timepoint is after hybridization of partially double stranded complex with recipient nucleic acids.

The following Examples are provided to illustrate, but not limit, the invention.

EXAMPLES

Example 1

Creating a Double Stranded cDNA with a 3' Overhang of a Unique Sequence Appended to the Second Strand cDNA from Poly-A mRNA Using a Single Composite Primer Poly-A mRNA from MOLT-4 cell line (CLONTECH 6587-1) was used. The process was in two steps: 1) synthesis of first cDNA strand; 2) synthesis of second cDNA strand and cleavage to produce a double stranded cDNA (with a 3' overhang or single stranded portion) from the total mRNA of the sample. The double stranded cDNA product comprises at one end an RNA/DNA heteroduplex, which is a substrate for RNase H. The sequence of the two strands of this heteroduplex portion is not related to the target, and is incorporated through utilization of a composite (first) primer.

Primer sequences:

```
MTA1: GACGGAUGCGGUCTTTTTTT      (SEQ ID NO:1)

MTA2: GACGGAUGCGGUCUTTTTTTTN    (SEQ ID NO:2)

MTA3: GACGGAUGCGGUCUTTTTTTTNN   (SEQ ID NO:3)
``` wherein italicized nucleotides denote ribonucleotides and "N" denotes a degenerate nucleotide (i.e., it can be A, T, C or G).

Step 1: Synthesis of the First Strand cDNA from Poly A mRNA 0.1 μg of total poly-A mRNA was mixed with the following reagents in a total volume of 10 ul:

0.2 μl primer MTA3 (100 μM)

0.5 μl dNTPs (25 mM)

0.1 μl Rnasin 0.1 μl DTT

2 μl 5×AMV reverse transcriptase reaction buffer

DEPC treated water to 10 μl total volume

The reaction mixture was incubated for 2 min at 75° C., and then cooled to 37° C. 1 μl AMV reverse transcriptase (USB 70041Y, 15 U/μl) was added to each reaction and the reaction mixture further incubated at this temperature for 60 min.

Step 2: Second Strand cDNA Synthesis and Cleavage to Generate a 3' Single Stranded Portion (Overhang)

The first strand cDNA reaction mixture was mixed with 10 μl of the second strand cDNA synthesis mixture containing the following:

1 μl 10× Klenow reaction buffer
0.1 μl dNTPs (25 mM)
0.5 μl Klenow (USB 2141Y 5 U/μl) DNA polymerase
0.1 μl of *E. coli* Ribonuclease H (BRL 18021-014, 4 U/μl
8.4 μl water The reaction mixture was incubated for 30 min at 37° C., followed by heating to 75° C. for 5 min to stop the reactions by inactivating the enzymes.

Example 2

Characterization of Products of Step 2 Reaction of Example 1

In the reaction of Example 1, a "unique" sequence (i.e., a sequence not hybridizable to the RNA template) is expected to be created at the 3'-end of the second strand cDNA due to the "unique" sequence of the 5' RNA portion of the composite primer used. This sequence (of the 3'-end of the second strand cDNA) is complementary to the 5'-RNA portion of the composite primer and is not related to sequences in the target RNA. To determine the presence of this sequence in the second strand cDNA that is obtained, PCR amplification of the reaction products (as found in reaction mix of step 2 of Example 1) was performed using a primer which is complementary to the expected sequence at the 3'-end of the second strand cDNA, as a forward primer, and a G3PDH-specific primer as a reverse PCR primer. This primer pair would be expected to amplify a specific product from a double stranded cDNA that has the "unique" sequence.

PCR reactions were carried out as follows:
Each 50 μl of PCR reaction contains:
0.4 μM of each primer (Biosource International)
100 μM of each dNTP (Epicenter)
2 mM Magnesium chloride (Epicenter)
1–2 units Polymerase (either MasterAmp taq or MasterAmp Tfl, both from Epicenter)
5 μl 10× buffer as supplied with the enzyme.

A 1:20 dilution of the cDNA generated in step 2 in Example 1.

The PCR amplification cycles were 94° C. for 30 seconds, 51° C. for 30 seconds, and 72° C. for 30 seconds. Generally, the samples were cycled 20 or 25 times. There was a final 5-minute extension at 72° C. before the samples were held at 4° C.

Similar experiments were carried out with primer specific to the T-cell receptor specific mRNA (TCR) which is expressed by the MOLT4 cell line.

Expected PCR product size (base pairs) using the G3PDH primers.

| REV PRIMER | FORWARD PRIMER G3PDH3 | FORWARD PRIMER dMTA1 |
| --- | --- | --- |
| G3PDH5-2 | 18 | 62 |
| G3PDH5-3 | 110 | 156 |
| G3PDH5-4 | 157 | 203 |
| G3PDH5 | 253 | 299 |
| G3PDH5-6 | 309 | 354 |
| G3PDH5-7 | 361 | 405 |

Primer Sequences

G3PDH5:   5'TTT CCT GGT ATG ACA ACG AA    (SEQ ID NO:4)

G3PDH5-4: 5'CCA GCA AGA GCA CAA GAG GA    (SEQ ID NO:5)

G3PDH3:   5'GAT GGT ACA TGA CAA GGT       (SEQ ID NO:6)

dMTA1:    5'GAC GGA TGC GGT CTT TTT TTT   (SEQ ID NO:7)

Expected PCR Product Size (Base Pairs) Using T-Cell Receptor Primers

|  | TCR3 | DMTA1 |
| --- | --- | --- |
| TCR5-2 | 160 | Approx. 440 |
| TCR5 | 238 | Approx. 500 |

Primer Sequences

TCR5:   5'CCC GCA ACC ACT TCC GCT GTC   (SEQ ID NO:8)

TCR5-2: 5'CAA ACC CGT CAC CCA GAT CGT   (SEQ ID NO:9)

TCR3:   5'CAA CAC AAG GGC GCT GAC C     (SEQ ID NO:10)

The results show that the unique sequence is incorporated into the second strand cDNA, as indicated by the presence of a product that was about 250 base pairs in length when the step 2 reaction mix was PCR amplified using primers DMTA1 and G3PDH5 (amplification of a sequence of G3PDH mRNA), and a product of about 400 base pairs in length when using primers DMTA1 and TCR5-2 (amplification of a sequence of TCR beta chain mRNA). Thus, the results demonstrated the incorporation of the "unique" sequence (of the RNA portion of the composite primer used in Example 1) into the partially double stranded cDNA products generated.

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention, which is delineated by the appended claims.

What is claimed is:

1. A method for generating a hybrid nucleic acid, said method comprising:
  (a) preparing a complex of first and second primer extension products said complex comprising a 3' single stranded portion, wherein said complex comprising a 3' single stranded portion is prepared according to a method comprising:
    (i) extending a first primer hybridized to a target RNA with an enzyme comprising RNA-dependent DNA polymerase activity, wherein the first primer is a composite primer comprising an RNA portion and a 3' DNA portion, whereby a complex comprising a first primer extension product and the target RNA is produced;
    (ii) cleaving target RNA in the complex of step (i);
    (iii) extending a second primer hybridized to the first primer extension product with an enzyme comprising DNA-dependent DNA polymerase activity and an enzyme comprising RNA-dependent DNA polymerase activity, whereby a second primer extension product is produced to form a complex of first and second primer extension products;
    (iv) cleaving RNA from the first primer in the complex of step (iii) with an enzyme that cleaves RNA from an RNA/DNA hybrid such that a complex comprising hybridized first and second primer extension products comprising a 3' single stranded portion is generated; and
  (b) hybridizing the 3' single stranded portion of the complex of first and second primer extension products with a recipient nucleic acid molecule; whereby a hybrid nucleic acid is generated.

2. The method of claim 1, further comprising: (c) generating a recombined nucleic acid from the hybrid nucleic acid.

3. The method of claim 1 or 2, wherein the second primer comprises a fragment of the target RNA hybridized to the primer extension product, said fragment generated by cleaving target RNA in the complex of step (a).

4. The method of claim 1 or 2, wherein the second primer comprises DNA.

5. The method of claim 1 or 2, wherein the RNA portion of the first primer is 5' with respect to the 3' DNA portion.

6. The method of claim 5, wherein the 5' RNA portion is adjacent to the 3' DNA portion.

7. The method of claim 1 or 2, wherein the target RNA is mRNA, and the first primer comprises a poly-dT sequence, and further comprises a 5' portion that does not hybridize to the target mRNA under conditions in which the first primer hybridizes to the target mRNA.

8. The method of claim 1 or 2, wherein the first primer comprises a random sequence.

9. The method of claim 1 or 2, wherein a plurality of different first primers are used for hybridizing to the target RNA.

10. The method of claim 1 or 2, wherein the RNA portion of the first primer comprises at least about 5 nucleotides and the DNA portion of the first primer comprises at least 1 nucleotide.

11. The method of claim 1 or 2, wherein the enzyme that cleaves RNA from an RNA/DNA hybrid is RNase H.

12. The method of claim 1 or 2, wherein the same enzyme comprises RNA-dependent DNA polymerase activity and cleaves RNA from an RNA/DNA hybrid.

13. The method of claim 1 or 2, wherein the same enzyme comprises DNA-dependent DNA polymerase activity and cleaves RNA from an RNA/DNA hybrid.

14. The method of claim 1 or 2, wherein the same enzyme comprises DNA-dependent DNA polymerase activity, RNA-dependent DNA polymerase activity and cleaves RNA from an RNA/DNA hybrid.

15. The method of claim 1 or 2, wherein different enzymes comprise RNA-dependent DNA polymerase activity and DNA-dependent DNA polymerase activity.

16. The method of claim 1 or 2, wherein different enzymes comprise RNA-dependent DNA polymerase activity and cleave RNA from an RNA/DNA hybrid.

17. The method of claim 1 or 2, wherein different enzymes comprise DNA-dependent DNA polymerase activity and cleave RNA from an RNA/DNA hybrid.

18. The method of claim 1 or 2, wherein different enzymes comprise DNA-dependent DNA polymerase activity, RNA-dependent DNA polymerase activity and cleave RNA from an RNA/DNA hybrid.

19. The method of claim 1 or 2, wherein the entire 3' single stranded portion of the complex is hybridized to the recipient molecule.

20. The method of claim 1 or 2, wherein a portion of the 3' single stranded portion of the complex is hybridized to the recipient molecule.

21. The method of claim 1 or 2, wherein cleaving target RNA in step (ii) is with an enzyme that cleaves RNA from an RNA/DNA hybrid.

22. The method of claim 21, wherein the enzyme is RNaseH.

23. The method of claim 2, wherein generating a recombined nucleic acid comprises ligation.

24. The method of claim 2, wherein generating a recombined nucleic acid comprises extension of a 3' end by an enzyme having DNA polymerase activity.

25. The method of claim 24, wherein the enzyme having DNA polymerase activity has strand displacement activity.

26. The method of claim 2, wherein generating a recombined nucleic acid comprises gap filling and ligation.

27. The method of claim 3, wherein cleavage is with an enzyme that cleaves RNA from an RNA/DNA hybrid.

28. The method of claim 27, wherein the enzyme is RNaseH.

29. A method of making a hybrid nucleic acid, said method comprising: hybridizing a 3' single stranded portion of a complex of first and second primer extension products with a recipient nucleic acid molecule, whereby a hybrid nucleic acid is generated, wherein said complex of first and second primer extension products is prepared according to a method comprising:
  (i) extending a first primer hybridized to a target RNA with an enzyme comprising RNA-dependent DNA polymerase activity, wherein the first primer is a composite primer comprising an RNA portion and a 3' DNA portion, whereby a complex comprising a first primer extension product and the target RNA is produced; (ii) cleaving target RNA in the complex of step (i); (iii) extending a second primer hybridized to the first primer extension product with an enzyme comprising DNA-dependent DNA polymerase activity and an enzyme comprising RNA-dependent polymerase activity, whereby a second primer extension product is produced to form a complex of first and second primer extension products; (iv) cleaving RNA from the first primer in the complex of step (iii) with an enzyme that cleaves RNA from an RNA/DNA hybrid such that a complex comprising hybridized first and second primer extension products comprising a 3' single stranded portion is generated.

30. The method of claim 10, wherein the RNA portion of the first primer consists of about 5 to about 50 nucleotides and the DNA portion of the first primer consists of about 1 to about 20 nucleotides.

31. The method of claim 1, wherein the hybrid nucleic acid is DNA.

32. The method of claim 29, wherein the hybrid nucleic acid is DNA.

* * * * *

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)...(14)
<223> OTHER INFORMATION: Ribonucleotide
<220> FEATURE:
<221> NAME/KEY: misc_feature
<222> LOCATION: (15)...(21)
<223> OTHER INFORMATION: Deoxyribonucleotide

<400> SEQUENCE: 1
gacggaugcg gucutttttt t                                              21

<210> SEQ ID NO 2
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)...(14)
<223> OTHER INFORMATION: Ribonucleotides
<220> FEATURE:
<221> NAME/KEY: misc_feature
<222> LOCATION: (15)...(22)
<223> OTHER INFORMATION: Deoxyribonucleotides
<220> FEATURE:
<221> NAME/KEY: misc_feature
<222> LOCATION: 22
<223> OTHER INFORMATION: n = A,T,C or G

<400> SEQUENCE: 2
gacggaugcg gucutttttt tn                                             22

<210> SEQ ID NO 3
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)...(14)
<223> OTHER INFORMATION: Ribonucleotides
<220> FEATURE:
<221> NAME/KEY: misc_feature
<222> LOCATION: (15)...(23)
<223> OTHER INFORMATION: Deoxyribonucleotide
<220> FEATURE:
<221> NAME/KEY: misc_feature
<222> LOCATION: 22, 23
<223> OTHER INFORMATION: n = A,T,C or G
```

```
<400> SEQUENCE: 3
gacggaugcg gucuuuuuuu tnn                                           23

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tttcctggta tgacaacgaa                                               20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ccagcaagag cacaagagga                                               20

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
gatggtacat gacaaggt                                                 18

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gacggatgcg gtcttttttt t                                             21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
cccgcaacca cttccgctgt c                                             21

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
caaacccgtc acccagatcg t                                             21

<210> SEQ ID NO 10
```

```
-continued

<211> LENGTH: 19
<212> TYPE: DNA
<213> ORGANISM: Artificial Sequence
<220> FEATURE:
<223> OTHER INFORMATION: Primer

<400> SEQUENCE: 10
caacacaagg gcgctgacc                                                    19
```